(12) United States Patent
Wilf et al.

(10) Patent No.: US 10,420,464 B2
(45) Date of Patent: Sep. 24, 2019

(54) GAZE TRACKING SYSTEM

(71) Applicant: Saar Wilf, Tel Aviv (IL)

(72) Inventors: Saar Wilf, Tel Aviv (IL); Alex Alon, Binyamina (IL)

( * ) Notice: Subject to any disclaimer, the term of this patent is extended or adjusted under 35 U.S.C. 154(b) by 282 days.

(21) Appl. No.: 14/904,703

(22) PCT Filed: Jul. 31, 2014

(86) PCT No.: PCT/IB2014/063586
§ 371 (c)(1),
(2) Date: Jan. 13, 2016

(87) PCT Pub. No.: WO2015/015454
PCT Pub. Date: Feb. 5, 2015

(65) Prior Publication Data
US 2016/0143528 A1    May 26, 2016

Related U.S. Application Data

(60) Provisional application No. 61/860,280, filed on Jul. 31, 2013.

(51) Int. Cl.
*A61B 3/113* (2006.01)
*A61B 3/00* (2006.01)
(Continued)

(52) U.S. Cl.
CPC ........... *A61B 3/113* (2013.01); *A61B 3/0025* (2013.01); *A61B 3/12* (2013.01); *A61B 3/14* (2013.01); *G02B 27/1066* (2013.01)

(58) Field of Classification Search
CPC ........... A61B 3/14; A61B 3/113; A61B 3/102; A61B 3/12; A61B 3/032; A61B 3/103; A61B 3/13; A61B 3/0025; A61B 3/0041; A61B 3/1005; A61B 3/0008; A61B 3/0033; A61B 3/0058; A61B 3/0091; A61B 3/1025; A61B 3/1225; A61B 3/117; G06T 2207/30041; G06T 7/0012; G06T 2207/10101; G06T 2207/30201; G06T 2207/10028; G06T 2207/30104; G06T 7/0016; G06T 7/11; G06T 7/248; G06T 11/003; G06T 11/60; G06T 2207/10016; G06T 2207/20182; G06T 2207/20221; A61F 2009/00851; A61F 2009/00846; A61F 2/1648; A61F 2/1656; A61F 2002/1681; A61F 2009/00853; A61F 2009/00863; A61F 2009/0087;
(Continued)

(56) References Cited

U.S. PATENT DOCUMENTS 5,532,784 A     7/1996  Nishimura et al.
8,235,529 B1 *  8/2012  Raffle .................... A61B 3/113
                                                        351/209
(Continued)

*Primary Examiner* — Evan P Dzierzynski
*Assistant Examiner* — Sharrief I Broome

(57) ABSTRACT

A method, including illuminating an eye with light from a light source (62) so as to cause a first image (80) of the light source to be formed on a retina (78) of the eye. The method also includes capturing the light returning from the retina with a sensor (148) so as to receive at least a portion of a second image (130) of the first image on the sensor, and analyzing a signal from the sensor in order to determine a gaze direction of the eye.

20 Claims, 15 Drawing Sheets

(51) Int. Cl.
*A61B 3/12* (2006.01)
*A61B 3/14* (2006.01)
*G02B 27/10* (2006.01)

(58) Field of Classification Search
CPC .. A61F 2009/00887; A61F 2009/00897; A61F 2/1618; A61F 2/1637; A61F 2/164; A61F 2/1645
See application file for complete search history.

(56) References Cited

U.S. PATENT DOCUMENTS

| | | | |
|---|---|---|---|
| 2011/0279666 A1* | 11/2011 | Strombom | A61B 3/113 348/78 |
| 2012/0019662 A1* | 1/2012 | Maltz | G06F 3/013 348/158 |
| 2012/0212399 A1* | 8/2012 | Border | G02B 27/017 345/8 |
| 2013/0077049 A1 | 3/2013 | Bohn | |
| 2013/0176533 A1 | 7/2013 | Raffle | |

* cited by examiner

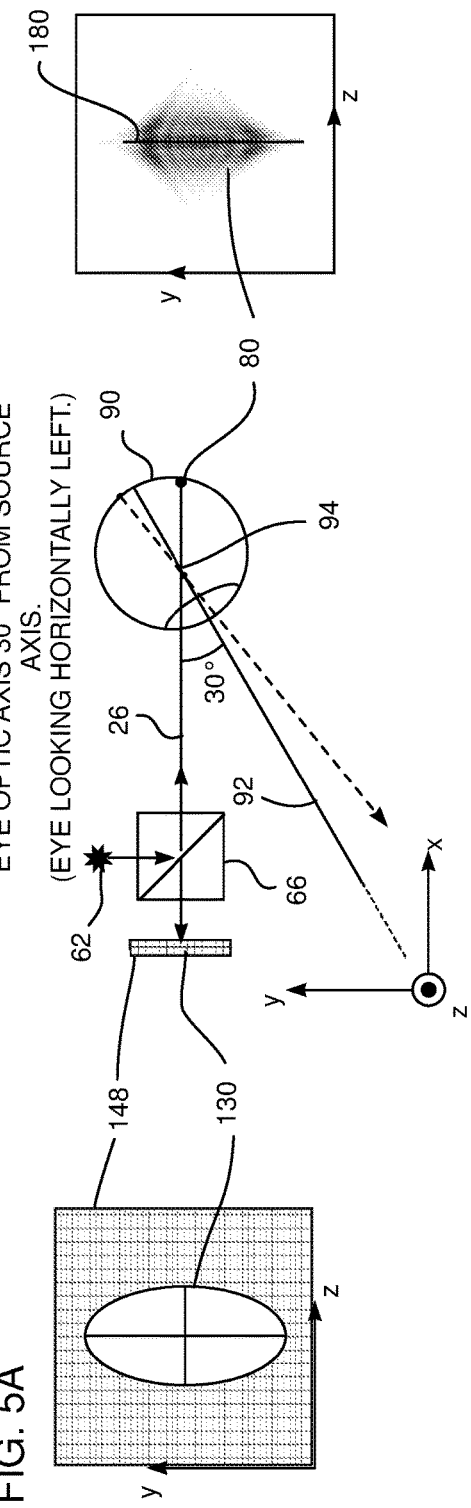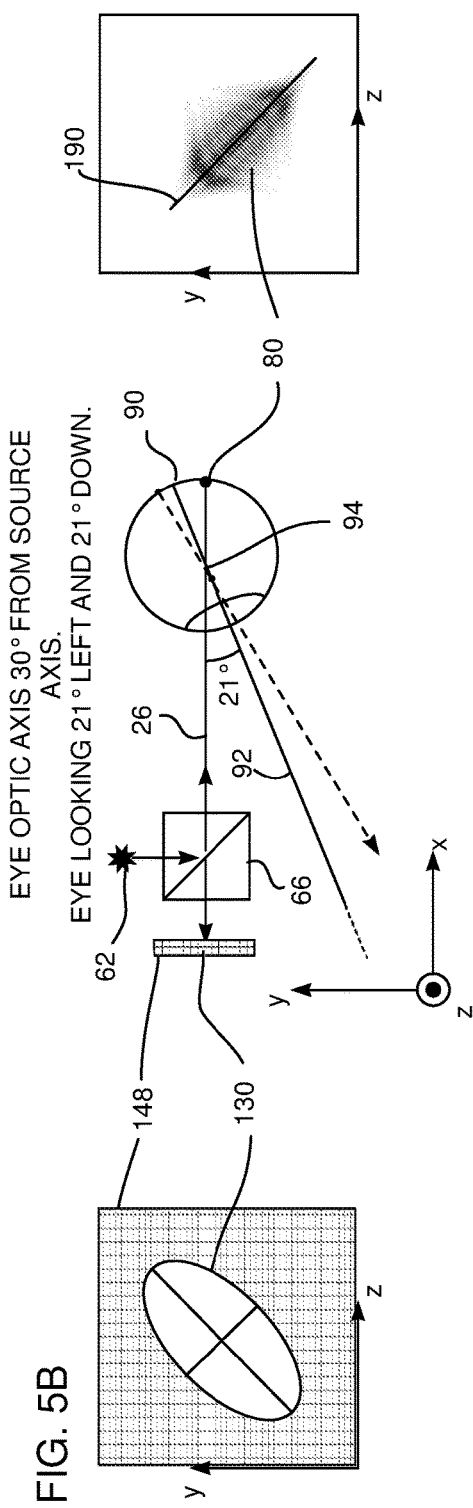

GAZE TRACKING SYSTEM

CROSS-REFERENCE TO RELATED APPLICATION

The present application claims the benefit of U. S. Provisional Patent Application 61/860,280, filed 31 Jul. 2013, which is incorporated herein by reference.

FIELD OF THE INVENTION

The present invention relates generally to tracking of the gaze direction of an eye, and specifically to tracking the direction using optical images returning from the eye.

BACKGROUND OF THE INVENTION

A gaze tracking system determines the direction an eye is looking at. A typical gaze tracking system uses a camera and a light source to acquire an image of the pupil and of a reflection from the cornea. Using the relative displacement of the corneal reflection with respect to the pupil enables a determination to be made of the gaze direction. Other methods, using optical and/or non-optical methods are also known. For example, other optical methods may track reflections from one or more of the surfaces of the lens of the eye. Non-optical methods may require the use of electrode patches placed near the eye, measuring potentials developed by the eye muscles as the eye changes its gaze direction. However, in many cases the measured gaze direction is relatively inaccurate. Specifically, systems that do not require the user to wear any device tend to be more inaccurate, and there is a need for an accurate gaze tracking system that does not require the user to wear anything.

Documents incorporated by reference in the present patent application are to be considered an integral part of the application except that to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

illuminating an eye with light from a light source so as to cause a first image of the light source to be formed on a retina of the eye;

capturing the light returning from the retina with a sensor so as to receive at least a portion of a second image of the first image on the sensor; and analyzing a signal from the sensor in order to determine a gaze direction of the eye.

Typically, the at least portion of the second image includes a partial second image.

Alternatively the at least portion of the second image includes a complete second image.

In a disclosed embodiment analyzing the signal includes determining at least one line of symmetry in the at least portion of the second image.

In a further disclosed embodiment analyzing the signal includes forming a correspondence between the at least portion of the second image and an ellipse, and determining the gaze direction includes determining the direction in response to at least one of an ellipticity of the ellipse and an orientation of an axis of the ellipse.

In a yet further disclosed embodiment capturing the light includes locating an aperture in proximity to the second image. The aperture may be larger than the second image. Alternatively, the aperture may be smaller than the second image. The method may include scanning at least one of the aperture and the light source so that the second image completely traverses the aperture.

Capturing the light may include forming multiple images of a pupil of the eye on the sensor using a plurality of lenslets, and analyzing the signal may include deriving the second image from the multiple images of the pupil.

In an alternative embodiment capturing the light includes forming a plurality of complete second images on the sensor using a plurality of lenslets, and analyzing the signal includes forming a composite second image from the plurality of complete second images. Typically the light source is in a plane defined by the plurality of lenslets.

In one embodiment capturing the light includes:

forming a single image including a pupil of the eye;

splitting the single image into a plurality of sub-images using a plurality of lenslets; and capturing the sub-images with the sensor, and analyzing the signal includes extracting the second image from at least one of the sub-images including the pupil.

In a further alternative embodiment capturing the light includes projecting a plurality of partial second images onto the sensor using a plurality of lenslets, and analyzing the signal includes forming a composite second image from the plurality of partial second images. Typically the light source is in a plane defined by the plurality of lenslets.

In a yet further alternative embodiment analyzing the signal includes forming a correspondence between image values of the second image and a function representative of the second image.

Typically, capturing the light includes using a focusing property of the eye to form the second image. There may be no lens positioned between the eye and the sensor.

In an alternative embodiment the method includes:

illuminating the eye with light from a further light source so as to cause a third image of the further light source to be formed on the retina of the eye; and capturing the light returning from the retina with the sensor so as to receive at least portion of a fourth image of the third image on the sensor and so as to generate a further signal, wherein analyzing the signal includes:

analyzing the signal and the further signal in order to determine the gaze direction of the eye.

There is further provided, according to an embodiment of the present invention a method, including:

illuminating a first eye of a subject with light from a light source so as to cause a first image of the light source to be formed on a first retina of the first eye;

illuminating a second eye of the subject with light from the light source so as to cause a second image of the light source to be formed on a second retina of the second eye;

capturing the light returning from the first retina with a sensor so as to receive at least a portion of a third image of the first image on the sensor, while blocking light returning from the second retina; and analyzing a signal from the sensor in order to determine a gaze direction of the first eye.

There is further provided, according to an embodiment of the present invention a method, including:

illuminating an eye with first light from a first light source so as to cause a first image of the first light source to be formed on a retina of the eye;

illuminating the eye with second light from a second light source so as to cause a second image of the second light source to be formed on the retina of the eye;

capturing the first light returning from the retina with a first sensor so as to receive at least a portion of a third image of the first image on the first sensor;

capturing the second light returning from the retina with a second sensor so as to receive at least a portion of a fourth image of the second image on the second sensor; and analyzing a first signal from the first sensor and a second signal from the second sensor in order to determine a gaze direction of the eye.

Typically analyzing the first and the second signals includes determining at least a first line of symmetry in the third image and at least a second line of symmetry in the fourth image. The method may also include deriving the gaze direction from an intersection of a first plane containing the first line of symmetry with a second plane containing the second line of symmetry. The method may also include deriving a gaze point of the eye from an intersection of the first line of symmetry with the second line of symmetry.

There is further provided, according to an embodiment of the present invention, apparatus, including:

a light source configured to illuminate an eye with light so as to cause a first image of the light source to be formed on a retina of the eye;

a sensor which is configured to capture light returning from the retina so as to receive at least a portion of a second image of the first image on the sensor; and a processor which is configured to analyze a signal from the sensor in order to determine a gaze direction of the eye.

There is further provided, according to an embodiment of the present invention, apparatus, including:

a light source configured to illuminate a first eye of a subject with light so as to cause a first image of the light source to be formed on a first retina of the first eye and to illuminate a second eye of the subject with light from the light source so as to cause a second image of the light source to be formed on a second retina of the second eye;

a sensor which is configured to capture the light returning from the first retina so as to receive at least a portion of a third image of the first image on the sensor, while light returning from the second retina is blocked from the image sensor; and a processor which is configured to analyze a signal from the sensor in order to determine a gaze direction of the first eye.

There is further provided, according to an embodiment of the present invention, apparatus, including:

a first light source configured to illuminate an eye with first light so as to cause a first image of the first light source to be formed on a retina of the eye;

a second light source configured to illuminate the eye with second light so as to cause a second image of the second light source to be formed on the retina of the eye;

a first sensor configured to capture the first light returning from the retina so as to receive at least a portion of a third image of the first image on the first sensor;

a second sensor configured to capture the second light returning from the retina so as to receive at least a portion of a fourth image of the second image on the second sensor; and a processor configured to analyze a first signal from the first sensor and a second signal from the second sensor in order to determine a gaze direction of the eye.

There is further provided, according to an embodiment of the present invention, apparatus, including:

an image sensor defining a sensor plane;

a plurality of lenslets located in proximity to the image sensor and arranged in a lenslet plane parallel to the sensor plane; and one or more light sources located in the lenslet plane.

Typically, the lenslets have a focal length selected so that an image of a subject illuminated by the light source is focused on the image sensor.

There is further provided, according to an embodiment of the present invention, apparatus, including:

an image sensor defining a sensor plane;

a plurality of lenslets located in proximity to the image sensor and arranged in a lenslet plane parallel to the sensor plane;

a partial reflector located in proximity to the plurality of lenslets; and a light source configured to transmit light to the partial reflector and located at a position that reflects in the partial reflector to the lenslet plane.

There is further provided, according to an embodiment of the present invention, apparatus, including:

a light source configured to illuminate an eye with light; and an image sensor configured to capture a light beam that has been focused by the eye and that returns undeviated from the eye.

Typically, there is no lens between the image sensor and the eye.

There is further provided a method, including:

illuminating an eye with light from a light source so as to cause a first image of the light source to be formed on a retina of the eye;

capturing the light returning from the retina with a sensor so as to form a second image of a pupil of the eye thereon; and analyzing a signal from the sensor including intensities measured over the second image of the pupil in order to determine a gaze direction of the eye.

Typically, analyzing the signal includes forming a correspondence between the intensities over the second image of the pupil and a function representative of the intensities.

The present invention will be more fully understood from the following detailed description of the embodiments thereof, taken together with the drawings in which:

BRIEF DESCRIPTION OF THE DRAWINGS

FIGS. 5A and 5B are schematic diagrams illustrating the derivation of the eye gaze direction in the system of FIG. 1, according to an embodiment of the present invention;

DETAILED DESCRIPTION OF EMBODIMENTS

Overview

Figure 1:
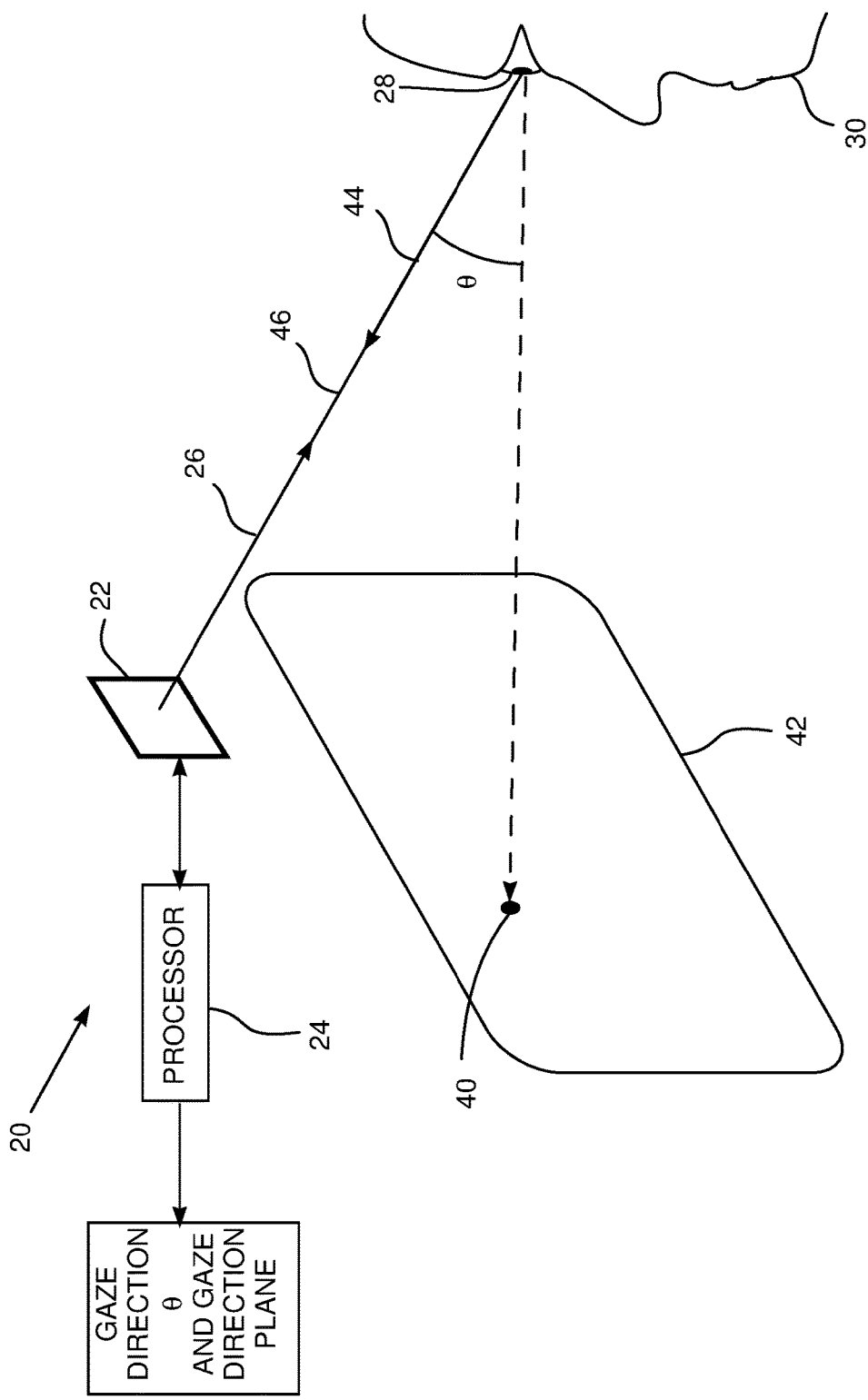
FIG. 1 is a schematic diagram illustrating operation of a gaze determining system, according to an embodiment of the present invention.

Embodiments of the present invention provide methods and systems for measuring the gaze direction of the eye of a subject. In order to measure the gaze direction, the eye is illuminated by light, typically invisible light such as near infra-red light, from a light source. The light source is typically small, projecting a diverging beam to the eye, and the eye focuses the beam to an image, herein termed a first image, of the source on the retina of the eye.

While most of the imaged light is absorbed by the retina, a portion is radiated from the retina to the pupil of the eye. This portion traverses the eye in a reverse direction, exiting the cornea of the eye as a converging beam which follows substantially the same path as the diverging beam from the light source. The converging beam is focused to a second image that is in generally the same location as the light source. The second image is also herein termed an eye reflection spot (ERS). The ERS is a real image of the first image formed on the retina, and the two images are at conjugate points that are in conjugate planes. (The conjugate properties are also true for the light source and the first image.)

In some embodiments the ERS may be focused onto an image sensor. Since the ERS is a real image, the sensor may be simply positioned at the location of the ERS, since the focusing is provided by the eye. Alternatively, one or more converging lenses may be positioned between the ERS and the second image to focus the ERS onto the sensor.

The eye is not an ideal lens, and so introduces aberrations into the first image of the light source that is formed on the retina. Similarly, the ERS has further aberrations that have been introduced by the light from the first image traversing the eye in the reverse direction. The aberrations depend on the angle made between the eye optic axis and the path of the converging (and diverging) beam. Typically, the larger the angle, the greater the aberrations.

The ERS is acquired by the image sensor, and the acquired image is analyzed. The gaze direction, which is related to (but not identical with) the optic axis, may be calculated from the aberrations introduced into the ERS.

The ERS aberrations, because of the properties of the eye, typically have at least one line of symmetry. In some embodiments the analysis of the ERS may identify the line of symmetry, and use this, together with other parameters derived from the analysis, to determine the gaze direction or gaze point. In alternative embodiments two ERSs are formed from two light sources, and the lines of symmetry may be used to find, by their intersection, a gaze point of the eye.

Detailed Description

In the following description, like elements in the drawings are identified by like numerals, and are differentiated as necessary by appending a letter to the identifying numeral or symbol.

FIG. 1 is a schematic diagram illustrating operation of a gaze determining system 20, according to an embodiment of the present invention. System 20 comprises a sensor assembly 22 which is coupled to a processor 24. In some embodiments assembly 22 incorporates processor 24, although in other embodiments the assembly and the processor are separate entities. The gaze determining system operates by sensor assembly 22 projecting light 26, typically non-visible light such as infrared light, towards an eye 28 of a subject 30. The subject is assumed, by way of example, to be looking at an object 40 on a screen 42, but it will be understood that system 20 is able to measure the direction in which the subject is looking, i.e., the subject's gaze direction, for substantially any viewed object.

As is explained in more detail below, eye 28 acts as a retro-reflector, so that some of projected light 26 returns back towards the sensor assembly as reflected light 44. Because of the retro-reflective properties of the eye, the projected light and the reflected light follow a common line 46. The reflected light is a convergent beam, converging to a real image. The sensor assembly receives the real image and generates signals in response to acquiring the real image, and the processor analyzes the signals. The analysis of the signals enables the processor to determine information about the gaze direction of eye 28 using one of the methods described below.

Figure 2:
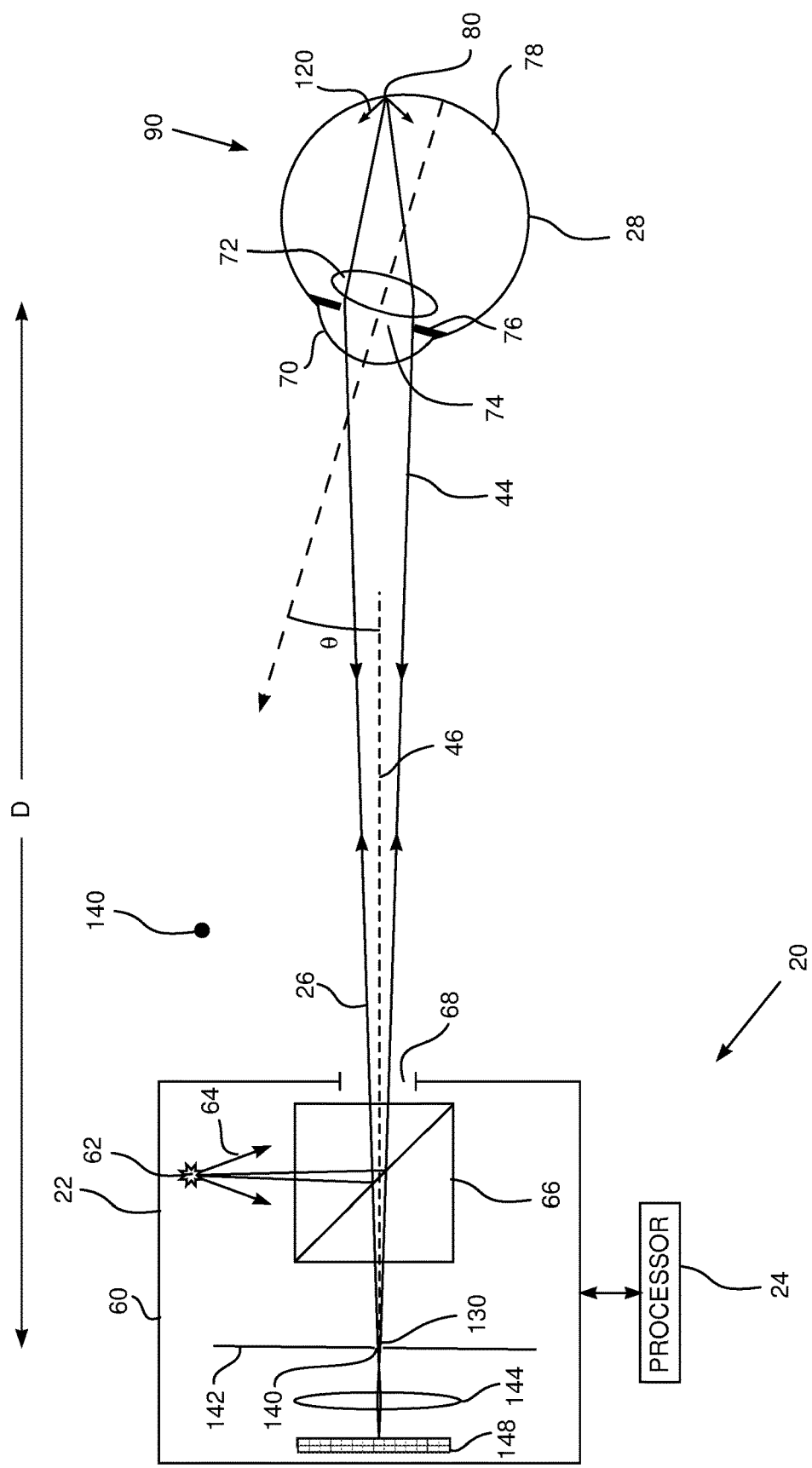
FIG. 2 is a schematic diagram of the system, according to an embodiment of the present invention.

FIG. 2 is a schematic diagram of system 20, according to an embodiment of the present invention. Elements of assembly 22 of the system are assumed to be housed in an enclosure 60, which is typically any convenient enclosure that, except for apertures described below, is light-tight. Assembly 22 comprises a light source 62 which is typically operative in the near infra-red region, for example at a wavelength of approximately 1000 nm. While embodiments of the present invention may use any convenient light source, from a signal analysis point of view it may be advantageous that the light source is as small as possible.

Such a small light source, may be implemented using a collimated laser that is focused by a lens, so as to produce a substantially point source. In some embodiments, the lens focusing the collimated laser has an f-number less than 2. Such a large aperture lens generates a substantially point source together with light radiating in a cone from the point source, the cone having a semi-angle greater than about 14°. In this case the cone may cover a circle of diameter greater than 35 cm at a distance from the light source of approximately 70 cm; 70 cm is a typical viewing distance from an eye looking at a computer monitor to the monitor.

Alternatively, the light source may be a small light emitting diode (LED). The inventors have found that so long as the light source is significantly smaller than the size of the eye reflection spot (ERS), described in detail below, embodiments of the present invention give good results for the measured gaze direction.

In the present disclosure, except where otherwise stated light source 62 is assumed to operate as a substantially point source, and those having ordinary skill in the art will be able to adapt the disclosure, mutatis mutandis, for distributed light sources.

Light from source 62 radiates as a divergent conical beam 64 which is reflected by a beam splitter 66. After reflection in the beam splitter, the divergent conical beam exits from enclosure 60 via a relatively narrow aperture 68 in the enclosure, and the size of the aperture is typically selected so that a region where eye 28 is expected to be is illuminated with reflected beam 64. Thus, after reflection in the beam splitter, beam 64 produces light 26, which is also a divergent beam. For clarity, only rays of beam 64 that reflect towards eye 28, i.e., light 26, are shown in the figure.

Eye 28 has a cornea 70, and an internal lens 72. Light entering the eye is limited by the size of an eye pupil 74 that is formed by an iris 76 of the eye, and the entering light is focused by the cornea and the internal lens (as well as by other transparent media in the eye) onto a retina 78 of the eye, so as to form a retinal image 80 of source 62. Taking the transparent elements of the eye together, the eye acts effectively as a convergent lens having a focal length of approximately 17 mm, although the focal length is changed, by changing the dimensions of internal lens 72, so as to focus on objects at different distances from the eye. In the description herein the effective convergent lens fanned by the eye is also referred to herein as eye lens 90.

Figure 3:
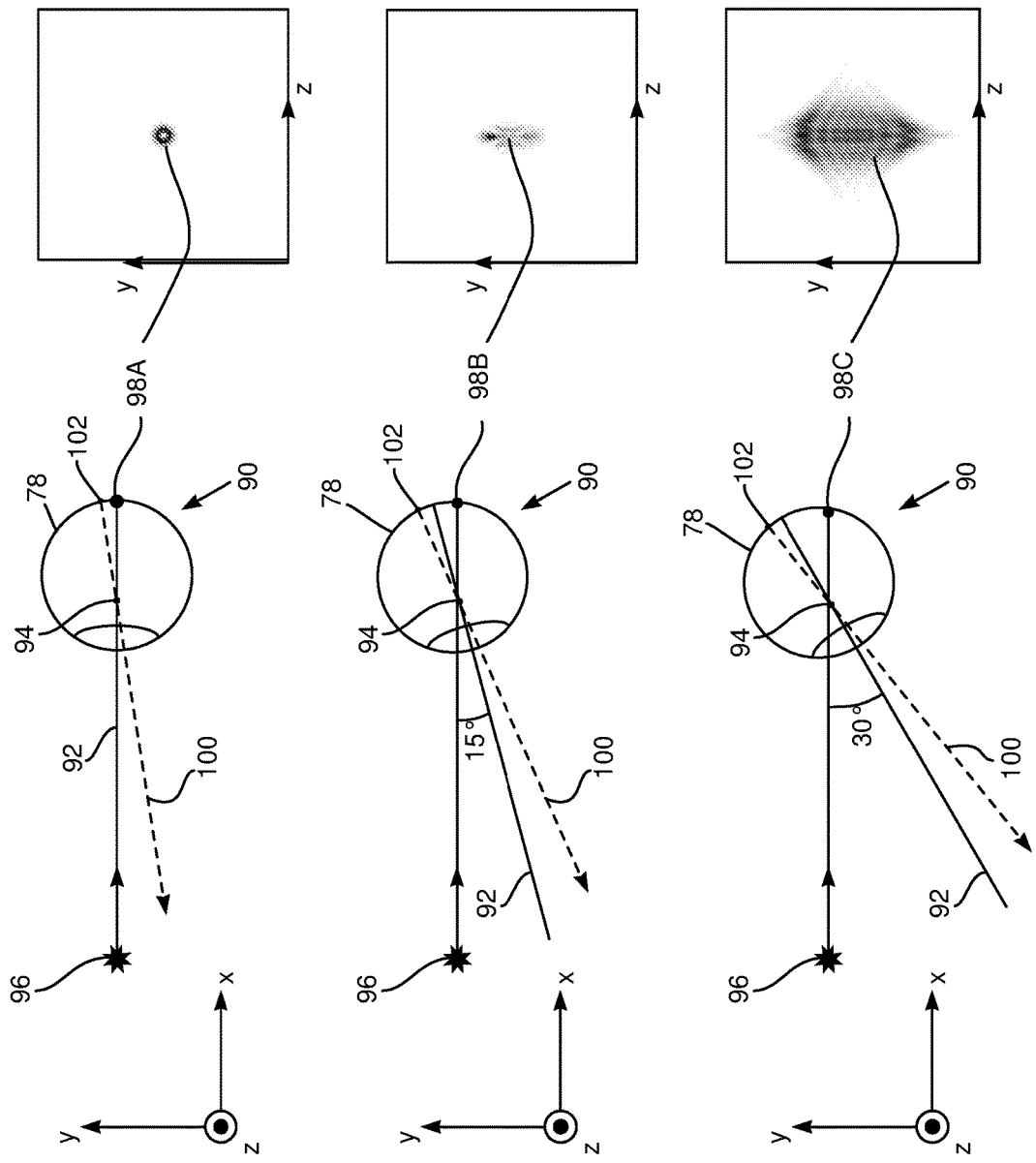
FIGS. 3A, 3B, 3C are schematic illustrations of an eye lens and of images generated by the lens, according to an embodiment of the present invention.

FIGS. 3A, 3B, 3C are schematic illustrations of eye lens 90 and of images generated by the lens, when the lens is in different orientations, according to an embodiment of the present invention. The depictions of eye lens 90 are of a horizontal cross-section of a right eye, and the view of the cross-section is from above. For clarity, the cross-sections have been drawn on sets of xyz axes, and the cross-sections are assumed to lie in the xy plane.

Eye lens 90 has an optical center 94, and a point source 96 radiates to the eye. A line from the point source to the optical center is assumed to be parallel to the x-axis. As for any practical lens, aberrations are introduced by the eye lens into retinal images focused by the lens. While the aberrations may be relatively small for retinal images formed on the optic axis of the eye lens, the aberrations increase in magnitude as objects and their retinal images subtend different angles with respect to the optic axis. The figures show simulated aberrated retinal images of point source 96 for the source at different angles to the eye lens optic axis. The simulated images are also referred to herein as point spread functions (PSFs).

FIG. 3A illustrates source 96 being on optic axis 92; FIG. 3B illustrates the source being at 15° to the optic axis; and FIG. 3C illustrates the source being at 30° to the optic axis.

For each of the situations illustrated in FIGS. 3A, 3B, 3C, the eye lens forms respective PSFs 98A, 98B, 98C, of source 96 on retina 78 of the eye. At the location of the retina where the PSFs are formed, the region of the retina is approximately a yz plane, and PSFs 98A, 98B, 98C, are also drawn on sets of yz axes.

As is apparent from PSFs 98B and 98C, the retinal images formed have a line of symmetry, in this case a line parallel to the y axis. In general, the line of symmetry of a PSF of a source is a line that is both in the plane of the PSF and is also in the plane defined by optic axis 92 and a line joining the source to optical center 94. The line of symmetry occurs because the latter plane is the only plane that contains source 96 and that intersects eye lens 90 symmetrically (assuming optic axis 92 does not intersect source 96). Therefore aberrations generated by the part of the lens on one side of this plane are generated in a mirror-image by the other part of the lens.

As is explained further in the description, embodiments of the present invention use a direction of a line of symmetry of an ERS, as well as analyzing the ERS, to calculate an angle between the eye lens optic axis and the source being imaged. The ERS is generated from a retinal PSF, and has a line of symmetry that is related to the line of symmetry of the PSF.

As is known in the art, the eye lens optic axis is not identical with a visual axis 100, corresponding to the gaze direction, of the eye. (In the present disclosure the terms visual axis and gaze direction are used interchangeably.) The visual axis of the eye is a line from a fovea 102 of the eye through optical center 94. The two axes, optic axis 92 and visual axis 100, are schematically drawn in the eye lenses of FIGS. 3A, 3B, 3C. Typically the two axes approximately lie in a common horizontal plane, and there is an approximately 5° separation of the axes, the fovea being further from the nose of a subject than the optic axis (this is true for both eyes). While the separation is typically substantially the same for both eyes of a given individual, there is typically a relatively large spread, in both a horizontal and a vertical direction, between different individuals.

As is also described below, embodiments of the present invention correct the calculated angle between the eye lens optic axis and the source being imaged, in order to account for the difference between the eye gaze direction and the eye lens optic axis.

Returning to FIG. 2, it will be understood that retinal image 80 is a PSF of source 62, and is also referred to herein as PSF 80. PSF 80 typically has dimensions of approximately 15 μm when the light source aligns with the optic axis of eye lens 90. While most of the light forming PSF 80 is absorbed by the retina (so generating the sensation of vision), some is radiated back from the retina as a divergent beam 120. A portion of beam 120 exits the eye as reflected light 44, following a similar path 46 to beam splitter 66 as is traversed by projected light 26. Reflected light 44 is a convergent beam, the optical elements of the eye acting to converge the reflected light, and is also referred to herein as beam 44.

Beam 44 traverses beam splitter 66 and converges to a spot 130, herein termed eye reflection spot (ERS) 130. ERS 130 is approximately located at a position corresponding to the reflection of source 62 in the beam splitter and is an image of retinal image 80. The exact position at which ERS 130 is located is determined by the effective focal lengths of eye 28 and of internal lens 72, which in turn depend on the distance from the eye to a gaze point 140 of the eye. While for simplicity and clarity beam 44 is shown as two rays converging to spot 130, it will be understood that because of the aberrations introduced by eye 28, cornea 70, and lens 72, the beam is comprised of multiple rays, within and outside the two rays shown in the figure. The multiple rays converge to a region corresponding to ERS 130.

ERS 130 is a real image of PSF 80, and the two images are at conjugate points of eye lens 90. It will be understood that since ERS 130 is formed by light traversing eye 28 in a forward and a reverse direction, the ERS has further aberrations compared to the aberrations of PSF 80. However, as for PSF 80, ERS 130 also has lines of symmetry which may be used to determine the gaze direction of the eye. If, as exemplified above, PSF 80 has dimensions of approximately 15 µm, ERS 130 has dimensions (caused by the magnification of the eye lens, as well as the added aberrations due to the retro-reflection) of approximately 1.2 mm. The inventors have found that the ERS may have dimensions up to approximately 10 mm to 15 mm (when the gaze angle is significantly large—so causing large aberrations).

An aperture 140 is located at the position of ERS 130, and a converging lens 144 focuses ERS 130 onto a rectangular sensor array 148. Substantially any array that has the size of the ERS and that is operative at the wavelength of the light source may be used. The sensor array captures an image of ERS 130, and for simplicity the captured image formed on the array is also referred to as ERS 130. (Array 148 is typically a single high resolution array, although in some embodiments array 148 may comprise a number of lower resolution arrays arranged to capture the ERS.) Processor 24 uses signals corresponding to the captured image to analyze the ERS, and from the analysis to determine information relating to gaze direction θ of eye 28. It will be understood that gaze direction θ is a two-dimensional angle.

Aperture 140 may be constructed from a controllable LCD (liquid crystal display) mask 142, which is operated by processor 24. In some embodiments, processor 24 adjusts the size of aperture 140 so that the whole of ERS 130 is transmitted to lens 144. Alternatively, the processor may configure the aperture size to be less than the ERS, and may move the small-sized aperture to effectively scan the ERS, each scan, of a portion of the ERS, being acquired by array 148. The processor may use the multiple scans of portions of the ERS to compile a complete ERS. Aperture 140 is typically operated to be as small as possible, while still allowing the whole ERS, or the ERS portion (whichever is being imaged) to pass, so as to reduce extraneous light from being imaged by array 148.

During operation of system 20, processor 24 may reposition and/or resize aperture 140 within mask 142. In order to implement such adjustments to the aperture, the processor typically uses an adaptive process which adjusts the aperture according to a tracked location of the eye and/or the ERS acquired by array 148. Such a process is described below with respect to FIG. 6.

Even with the presence of aperture 140, array 148 typically captures light from entities other than the ERS (i.e., not originating from pupil 74), such as ambient light from the subject's face and parts of the eye such as the iris and the sclera. Such captured light acts as noise in system 20. An embodiment of the present invention reduces the noise by moving source 62 or aperture 140, and capturing a first image from array 148 while the source is aligned with the aperture, and a second image while the source is slightly mis-aligned with the aperture. In the second image, the ERS falls on the mask, while the remaining reflected light is not significantly affected. Subtracting the two images substantially increases the signal-noise ratio of the ERS. Alternatively, a similar effect to that achieved by moving source 62 may be accomplished by switching between two light sources. Other methods for reducing the noise on array 148 will be apparent to those having ordinary skill in the art, and all such methods are included in the scope of the present invention.

The Eye Reflection Spot (ERS)

As stated above, processor 24 analyzes the ERS and uses parameters from the analysis to determine the gaze direction. Factors affecting the ERS include, but are not limited to, the following.

a) The size of the light source (source 62 in FIG. 2, source 96 in FIGS. 3A-3C). Typically, a small light source creates an ERS which may be easier to analyze than the ERS from an extended source. Because of the convolution process involved in formation of the ERS, a larger source increases the blur, or spread, of the ERS.

b) The direction of the light source relative to optic axis 92. A lens normally generates the least aberrations for images formed on its optic axis, and exhibits stronger aberrations as images increase their angular distance from the axis. Thus the ERS (as well as retinal image 80) typically exhibits asymmetric distortions related to the direction of the light source with respect to the optic axis, and the distortions increase as the distance to the axis increases.

As is explained further below with reference to FIGS. 5A and 5B, the ERS distortions typically have lines of symmetry corresponding to the axes of an ellipse.

c) The optical power of internal lens 72 affects the spread or blur, and to a lesser extent the size, of the ERS. For a given light source, the blur and size of the ERS are typically a minimum if the internal lens power corresponds to the eye being focused to the distance of the light source. If the power is larger (eye focused closer than the light source distance) or smaller (eye focused farther than the light source distance), the blur and size of the ERS are typically larger than the minimum size. The size of the ERS, (in elliptical format) is considered further below with reference to FIGS. 5A and 5B.

d) The location on the retina of retinal image 80. Some areas of the retina reflect light better than others. For example, the optic disc (the region where the optic nerve connects to the eye) reflects more light than other areas, and creates a brighter ERS.

e) The size of eye pupil 74. A larger pupil causes a brighter ERS since more light enters eye 28 to form a brighter retinal image 80. In addition, more light is reflected back, from the retinal image, through the pupil to form the ERS. The size of pupil 74 also affects the aberrations in the ERS, since a larger pupil causes stronger aberrations because more of cornea 70 and internal lens 72 are used. Stronger ERS aberrations in turn cause a larger ERS.

f) Eyewear. Corrective eyewear introduces effects similar to those of cornea 70 and internal lens 72. Sunglasses reduce the ERS brightness. For simplicity, these types of eyewear are not considered further in the present disclosure, but those having ordinary skill in the art will be able to adapt the description, mutatis mutandis, to allow for a subject using eyewear.

g) A distance D (FIG. 2) between light source 62 (or its image in the beam splitter) and eye 28. The retinal image of the light source is magnified at the light source/ERS plane, corresponding to the location of ERS 130, by a magnification ratio $$M = \frac{D}{f},$$

where f is the eye's lens focal length. For a typical distance of D=70 cm and f≅17 mm, M≅40, Distance D is considered further below with reference to FIGS. 5A and 5B.

h) The wavelength emitted by light source 62.

Some of the factors affecting the ERS are described in more detail below.

Figure 4:
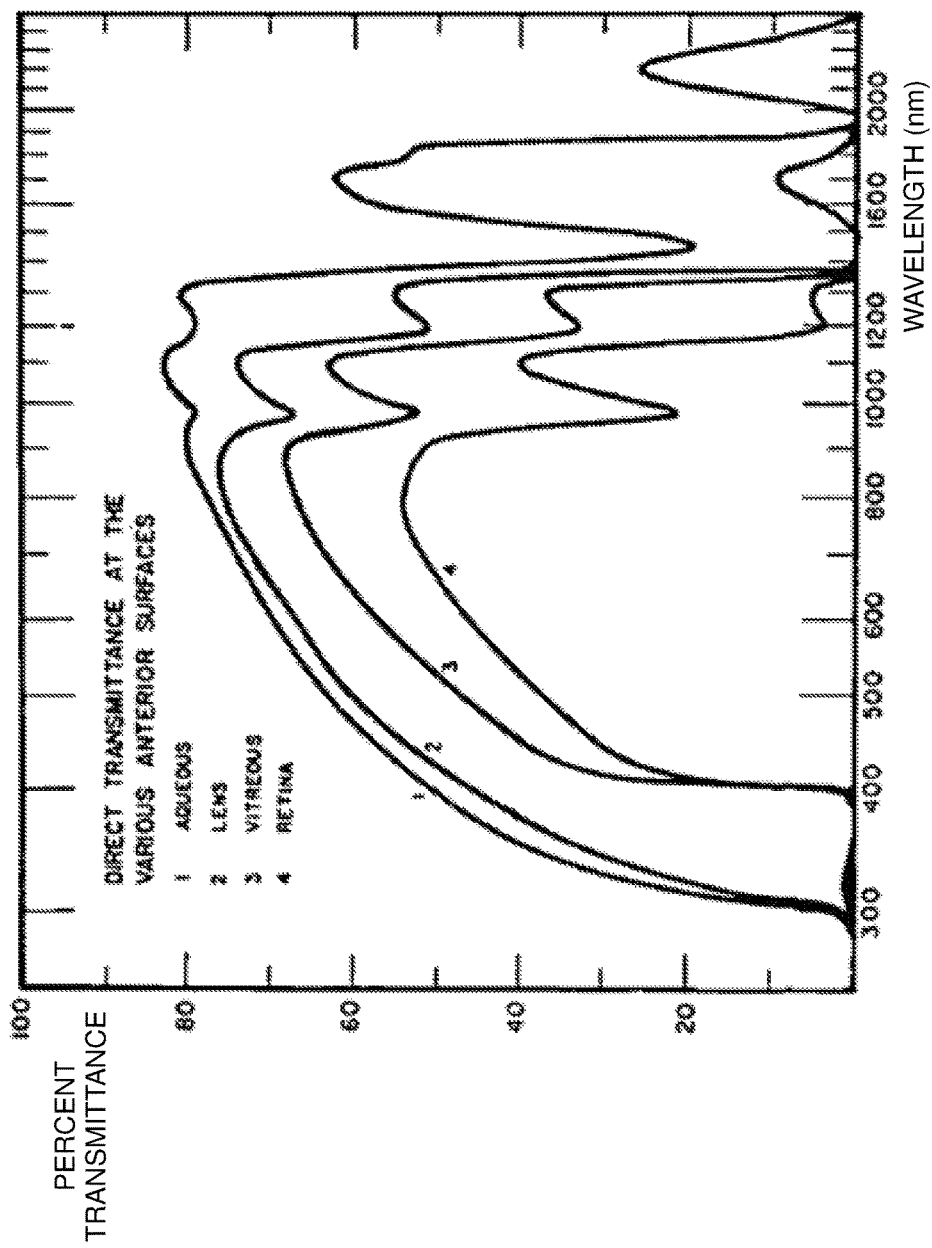
FIG. 4 shows graphs of transmission of ocular media at various wave lengths, according to an embodiment of the present invention.

FIG. 4 shows graphs of transmission to different surfaces of the eye at various wave lengths. With reference to factor h) above, as is seen from the graphs, a brightest retinal image 80 and a brightest ERS 130 is formed when light source 62 operates at a near infra-red wavelength of approximately 800 nm.

FIGS. 5A and 5B are schematic diagrams illustrating the derivation of the eye gaze direction in system 20, according to an embodiment of the present invention. For simplicity, not all elements of system 20 that are shown in FIG. 2 are drawn in FIGS. 5A and 5B. The elements of system 20 have been drawn on a set of xyz orthogonal axes, where the edges of sensor array 148 define the orthogonal y and z axes and wherein the array lies in a yz plane. The elements are shown projected onto an xy plane and light 26 from source 62, passing through optical center 94 of eye lens 90, is assumed to be parallel to the x axis. Projected light 26, which is a line from the reflection of source 62 in beam splitter 66 to optical center 94, is herein also termed source axis 26. The figures illustrate a horizontal cross-section of eye lens 90, (similar to the depictions of FIGS. 3A, 3B, and 3C described above) and the eye is assumed to be looking so that its optic axis 92 is 30° from the source axis.

In FIG. 5A the eye is looking horizontally left, so that the eye optic axis may be considered to have rotated counter clockwise in the xy plane by 30°. In FIG. 5B the eye optic axis has rotated approximately 21° left and the same angular distance down (so giving a resultant rotation of 30°). In both cases retinal image 80 has a single line of symmetry, a line 180 in FIG. 5A, and a line 190 in FIG. 5B. The light from retinal image 80, that forms ERS 130, has been retro-reflected via eye lens 90, so that further aberrations have been introduced into the ERS. In consequence of the initial transmission and following retro-reflection the ERS has two orthogonal lines of symmetry, corresponding to the major and minor axes of an ellipse. In both figures the image of the ERS on array 148 has been drawn schematically as an ellipse. Because the eye is rotated from the source axis by the same angular rotation of 30°, the two ellipses are substantially congruent, although they have different orientations.

In both figures there is a plane, herein termed the source plane, defined by the major axis of the ellipse and the source light projection line (since the optic center of the eye is on the latter line, the optic center is on the source plane). The source projection line corresponds to source axis 26, defined above. Because the symmetry properties of the eye lens define the direction of the ellipse major axis, the eye optic axis is also in the source plane. Thus, in the situation illustrated in FIG. 5A, the eye optic axis is in an xy plane, which corresponds to the source plane. In the situation illustrated in FIG. 5B, the eye optic axis is in a plane that parallels the x axis, and that is approximately 45° from both the y and z axes; this plane corresponds to the source plane.

In some embodiments, depending on the focused distance of the eye lens, the source plane is defined by the minor axis of the ellipse and the source light projection line. Which axis of the ellipse defines the source plane is typically apparent by being the axis which defines the direction of the eye optic axis as being within an expected range of directions. For simplicity, in the present disclosure the source plane is assumed to be defined by the ellipse major axis and source light projection line, and those having ordinary skill in the art will be able to adapt the disclosure, mutatis mutandis, for the case of the source plane being defined by the minor ellipse axis and the source light projection line.

The ellipticity of the ellipse, i.e., the ratio between the major and minor axis, provides a measure of the angle θ subtended by the eye optic axis with the source axis, because typically the larger the angle θ, the larger the aberrations. Thus, the larger the ellipticity (corresponding to larger aberrations), the larger the angle between the eye optic axis and the source axis.

For a given angle between the eye optic axis and the source axis, the size of the ellipse depends on both the distance D between the light source and the eye, and to a lesser extent on the distance between the gaze point and the eye—the gaze distance (the latter has a greater effect on the blur of the ERS). Increasing D increases the size of the ellipse. For a given distance D, the ellipse size is a minimum if the gaze distance is D, and increases above the minimum if the gaze distance is larger or smaller than D.

It will be understood that by measuring the above properties of the ERS ellipse, i.e., the ellipse orientation, ellipticity, and size, the processor of system 20 is able to quantify the orientation of the eye optic axis. It will also be understood that in order to perform the quantification, not all of the ERS needs to be imaged on sensor array 148, since the ellipse parameters can be determined if only a portion of the ERS is imaged on the array.

Typically, the processor is able to perform the quantification by having subject 30 (FIG. 1) perform a simple calibration procedure such as gazing at specific points on screen 42. In the case of distance D, the calibration procedure may be implemented by having sensor 148 placed adjacent to screen 142 and measuring the size of the ellipse. Alternatively or additionally, other independent methods that are well known in the art (such as stereoscopic imagery), may be used for measuring distance D.

Such a calibration procedure as is referred to above may also be used to correct for differences between the eye optic axis and the eye gaze direction (referred to above with reference to FIGS. 3A, 3B, 3C). The calibration procedure may typically include measurements of head distance from screen 42 and/or orientation of the head with respect to the screen, and these measurements may be made by any convenient method known in the art, such as using two cameras in a stereoscopic configuration.

Alternatively, the gaze direction may be assumed to be a fixed angular distance from the optic axis, in which case measurements of head distance and orientation may be applied to evaluate the gaze direction from the measured optic axis.

Figure 6:
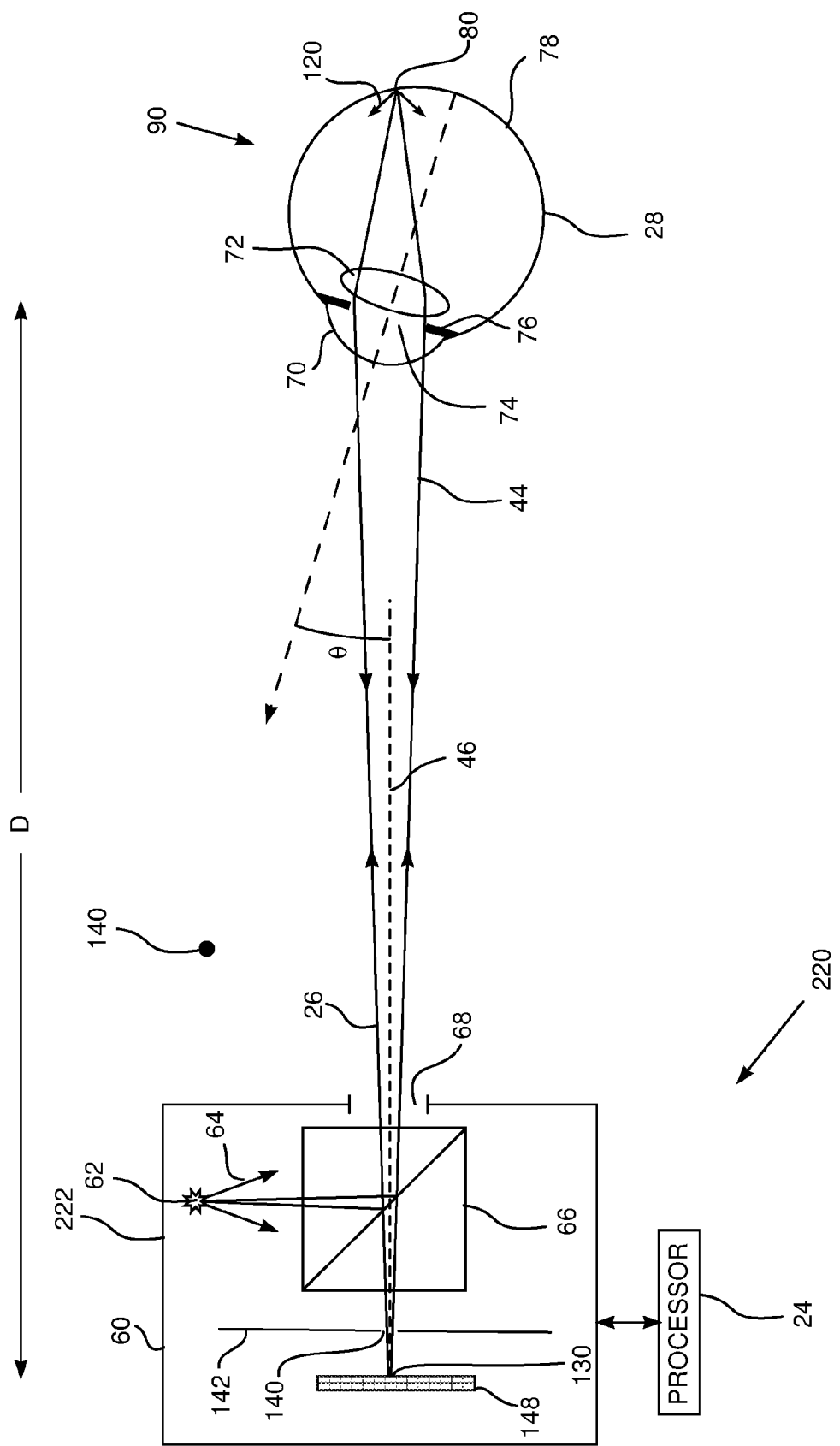
FIG. 6 is a schematic diagram of a gaze determining system, according to an alternative embodiment of the present invention.

FIG. 6 is a schematic diagram of a gaze determining system 220, according to an embodiment of the present invention. System 220 comprises a sensor assembly 222. Apart from the differences described below, the operations of system 220 and assembly 222 are generally similar to that of system 20 (FIGS. 1 to 5B), and elements indicated by the same reference numerals in both systems 20 and 220 are generally similar in construction and in operation.

In contrast to system 20, assembly 222 in system 220 does not comprise a converging lens 144. Rather, ERS 130 is imaged directly onto sensor array 148 so that no converging lens 144 is needed, and the image is acquired and analyzed by processor 24 substantially as described above for system 20. As for system 29, in system 220 aperture 140 performs the same function of reducing extraneous light from being imaged by array 148. However, in system 220 the aperture is not located at the ERS location, but is positioned some-what in front of array 148, thereby allowing the ERS to be imaged directly onto array 148.

Typically, an adaptive process, whereby aperture 140 is repositioned and/or resized according to the ERS acquired by array 148, is implemented. Such an adaptive process accommodates movement of pupil 74 with respect to array 148, the movement typically being caused by lateral motion of subject 30.

Figure 7:
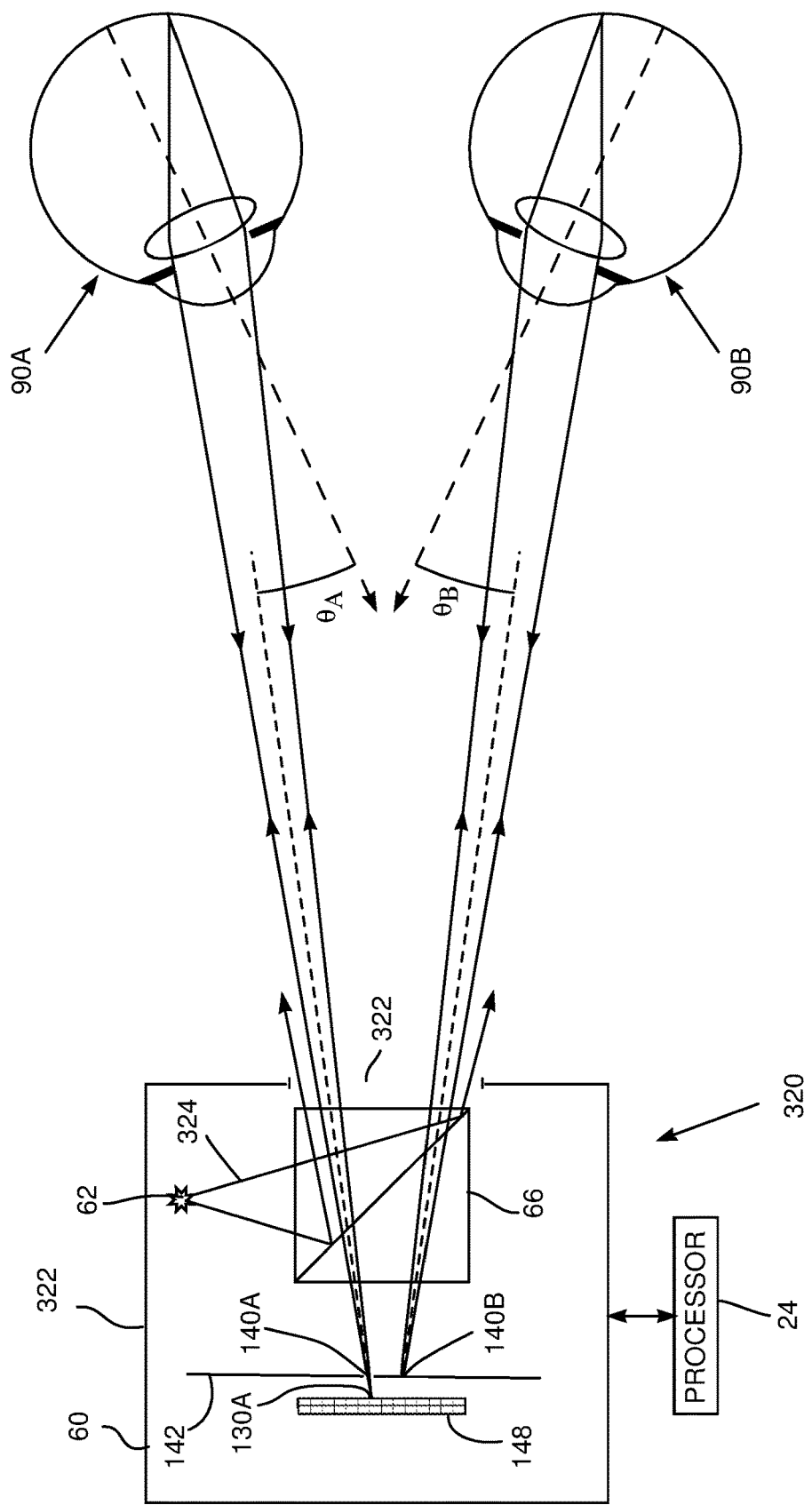
FIG. 7 is a schematic diagram of a gaze determining system, according to a further alternative embodiment of the present invention.

FIG. 7 is a schematic diagram of a gaze determining system 320, according to an embodiment of the present invention. System 320 comprises a sensor assembly 322, and apart from the differences described below, the operations of system 320 and assembly 322 are generally similar to that of system 220 (FIGS. 1 to 6), and elements indicated by the same reference numerals in both systems 220 and 320 are generally similar in construction and in operation.

In contrast to system 220, assembly 322 in system 320 may use a larger divergent beam 324 than divergent beam 64, and a larger aperture 322, compared to relatively narrow aperture 68, in enclosure 60. The larger aperture enables divergent beam 324, after reflection in beam splitter 66, to illuminate both left and right eye lenses. In the following description corresponding elements associated with different eyes are differentiated by appending a letter to the identifying element. Thus there is a right eye lens 90A and a left eye lens 90B. Both eye lenses act as retro-reflectors of light from source 62, so that an ERS from each eye could be imaged on sensor array 148.

Typically, processor 24 may operate mask 142 so that only one ERS is imaged at array 148 at a time. For example, as illustrated in the figure, at a given time mask 142 may be configured to have an aperture 140A open, allowing array 148 to acquire ERS 130A generated by eye lens 90A, while the mask blocks an aperture 140B, preventing the array from imaging an ERS of eye lens 90B. By toggling apertures 140A and 140B between open and closed states, the processor is able to acquire and analyze ERSs from both eyes, and so, as is described above for system 220, is able to estimate a gaze direction $\theta_A$ for right eye lens 90A and a gaze direction $\theta_B$ for left eye lens 90B.

In order to effectively block only one of the ERSs, apertures 140A and 140B should typically be separated by at least approximately 10 mm, to avoid the two ERSs overlapping. In this case, for a value of D=70 cm, and assuming an inter-pupillary distance of 7 cm, mask 142 should be separated from sensor 148 by about 10 cm.

Typically, aperture 322 has large enough dimensions so as to be able to accommodate movement of subject 30 in space (with consequent movement of the ERSs on array 148). Apertures 140A and 140B aperture 140 are typically repositioned and/or resized adaptively, according to the respective ERSs acquired by array 148. The adaptation may be implemented by receiving information from another camera that reports the direction of each of the pupils in space, or by iteratively changing the aperture until an ERS is located.

Figure 8:
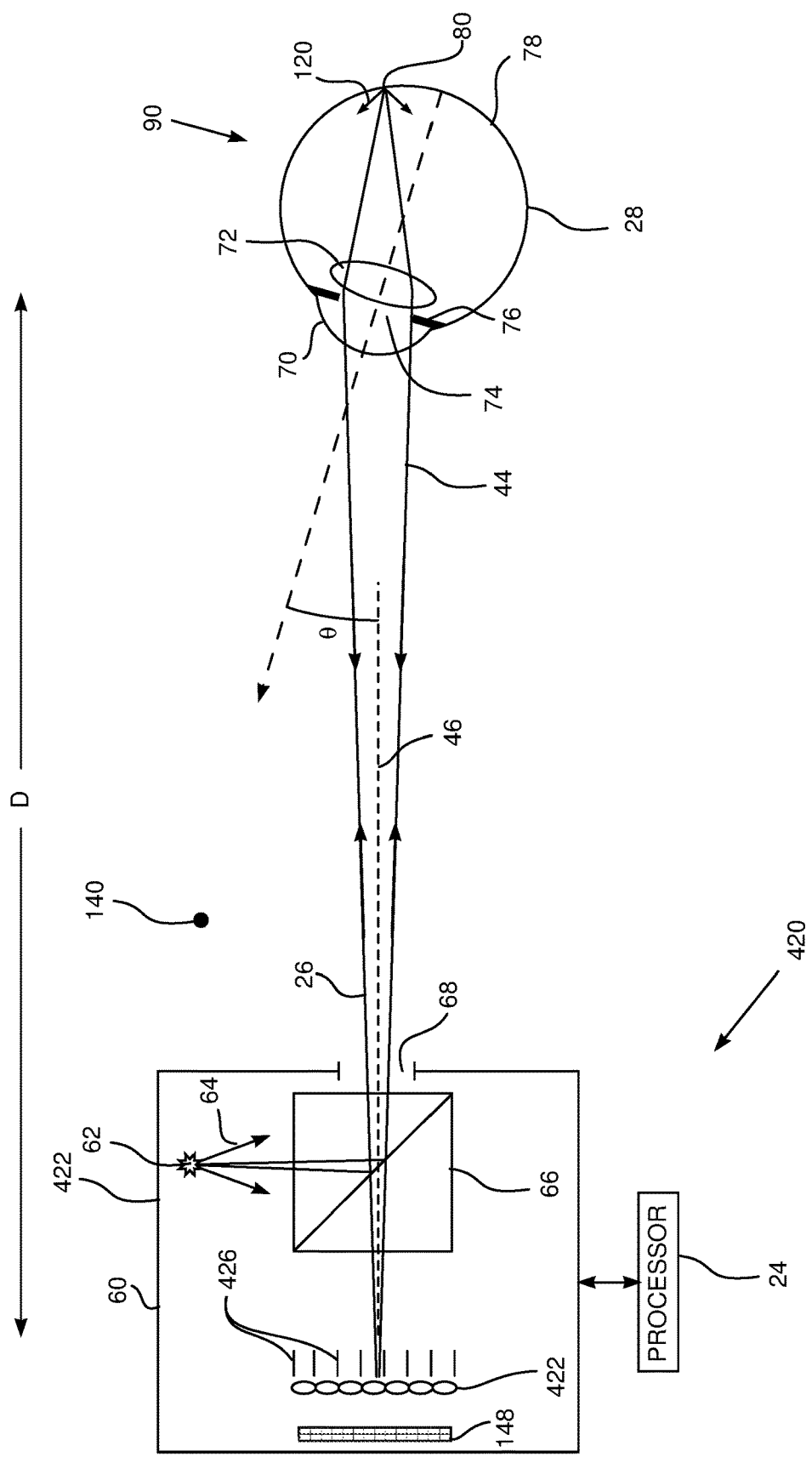
FIG. 8 is a schematic diagram of a gaze determining system, according to a yet further embodiment of the present invention.

FIG. 8 is a schematic diagram of a gaze determining system 420, according to an embodiment of the present invention. System 420 comprises a sensor assembly 422, and apart from the differences described below, the operation of system 420 is generally similar to that of system 20 (FIGS. 1 to 5B), and elements indicated by the same reference numerals in both systems 20 and 420 are generally similar in construction and in operation.

In assembly 422 converging lens 144 has been replaced by a lenslet array 422, and mask 142 has been replaced by optional multiple dividers 426. Dividers 426 are located adjacent to array 422, and are perpendicular to the array.

Rather than the single image of ERS 130 formed on sensor array 148 in system 20, the lenslet array forms multiple complete images of at least a portion of subject 30, including the subject's eye, and the dividers reduce leakage between the multiple images. Processor 24 may generate a resultant ERS by analyzing the multiple complete images, extracting subject's 30 pupil from each image, and merging them into an ERS image. Using multiple complete images enables the processor to separate the ERSs from other light entering aperture 68, such as light reflected from the face of subject 30.

In one embodiment a typical lenslet array is formed as a 10 mm square of lenslets arranged in a 33×33 array, each lenslet having a focal length of 2 mm, and the pitch of the array is approximately 300 µm. However, any other suitable array of lenslets may be used. Considerations in choosing the lenslet array specifications include the required resolution for each image, the required resolution for the ERS, the required field of view for the system, and the sensitivity of the system to overlap between images of neighboring lenslets.

Figure 9:
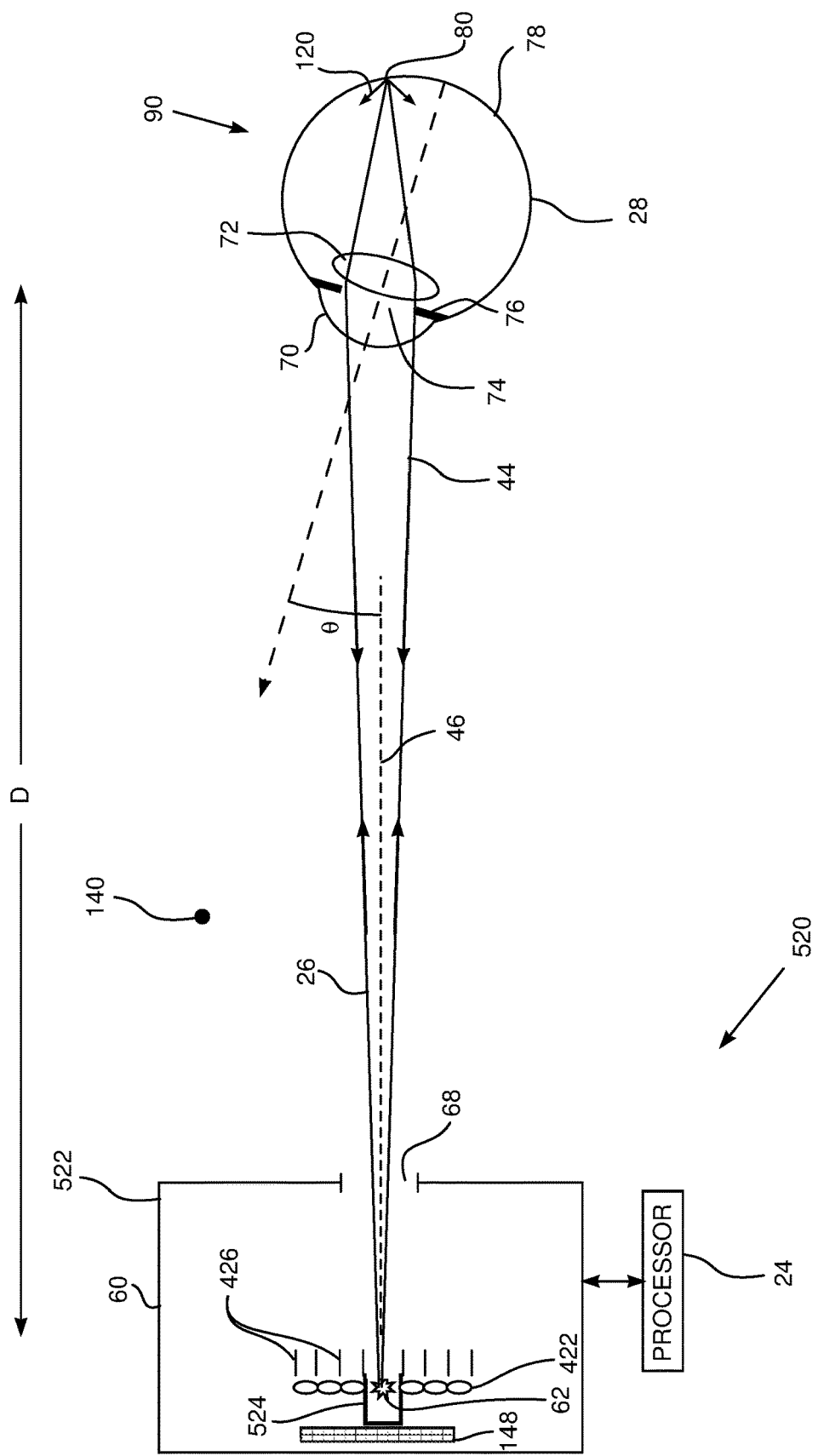
FIG. 9 is a schematic diagram of a gaze determining system, according to another embodiment of the present invention.

FIG. 9 is a schematic diagram of a gaze determining system 520, according to an embodiment of the present invention. System 520 comprises a sensor assembly 522. Apart from the differences described below, the operation of system 520 and assembly 522 is generally similar to that of system 420 (FIGS. 1 to 5B, and 8), and elements indicated by the same reference numerals in both systems 420 and 520 are generally similar in construction and in operation.

System 520 does not use a beam splitter. In assembly 522 source 62 is located approximately in the plane of lenslet array 422, so that the light from eye lens 90 converges to the plane of the array. The source is typically enclosed in a housing 524 which permits the source to directly transmit projecting light 26, obviating the need for beam splitter 66. Housing 524 is configured to prevent light from source 62 being projected directly onto sensor 148. As for system 420, lenslets in array 422 project multiple complete images of at least a portion of subject 30 onto array 148, and dividers 426 reduce leakage between the multiple images. While system 520 may not acquire a central portion of the ERS, the system may be implemented to be both smaller and cheaper than other systems described herein, such as system 420, while still extracting the parameters of the ERS needed to find the gaze direction.

System 520, as well as systems 20, 220, 320, and 420, project one or more substantially complete images of ERS 130 onto array 148, and processor 24 analyzes the single acquired complete image, or a sum of the multiple complete images. The analysis produces the parameters described of the ERS, i.e., the orientation, the size, and the ellipticity of the ERS considered as an ellipse, and thus the gaze direction of the eye.

Figure 10:
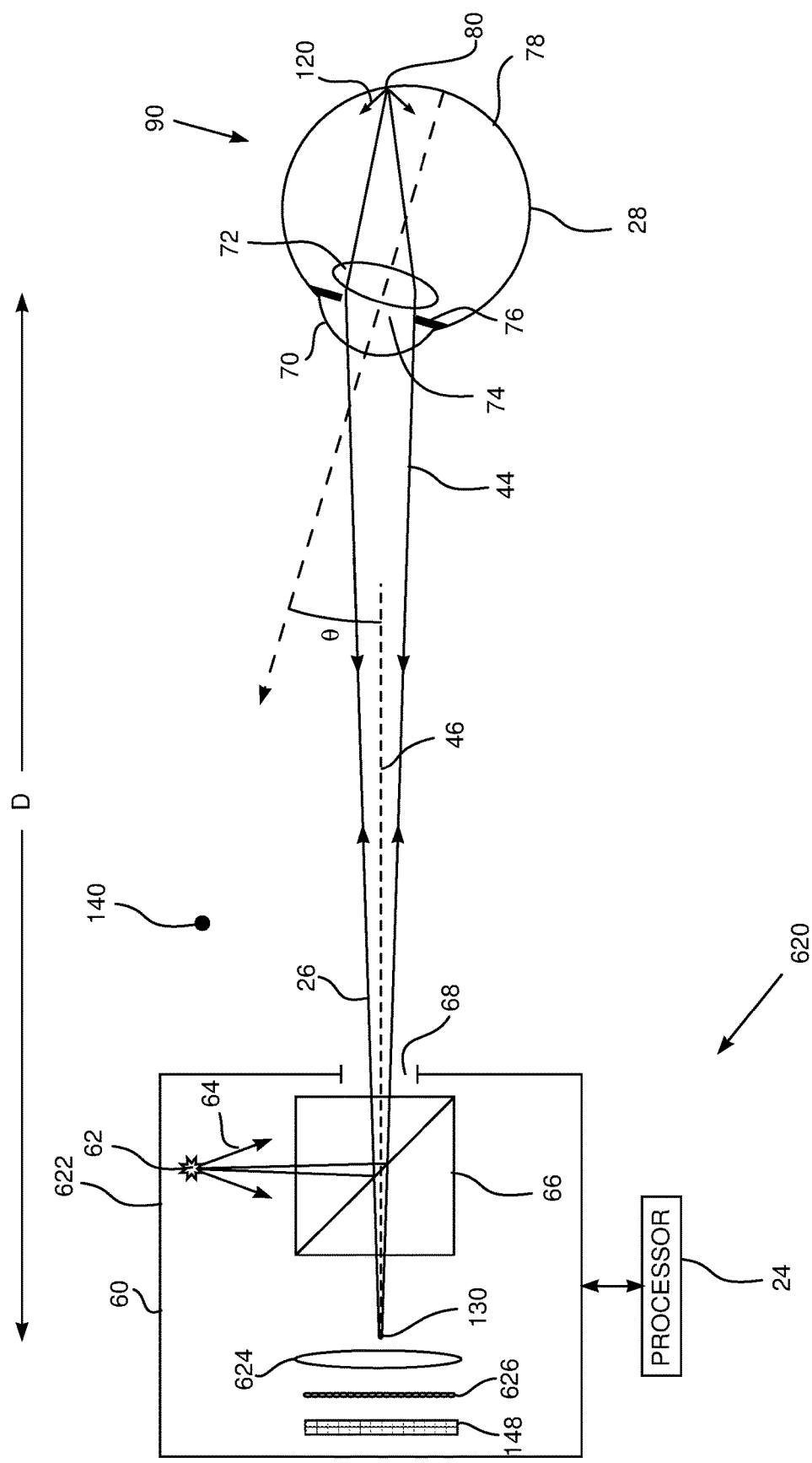
FIG. 10 is a schematic diagram of a gaze determining system, according to yet another embodiment of the present invention.

FIG. 10 is a schematic diagram of a gaze determining system 620, according to an embodiment of the present invention. System 620 comprises a sensor assembly 622, and apart from the differences described below, the operation of system 620 and assembly 622 is generally similar to that of system 20, and elements indicated by the same reference numerals in both systems 20 and 620 are generally similar in construction and in operation.

System 620 is substantially a plenoptic camera, in which a main lens 624 creates an image of the subject, including pupil 74, and the surroundings, on a lenslet array 626, and then each lenslet in the array splits its part of the image so as to form a plurality of sub-mages which are captured by image sensor 148, so that the signal for each pixel of image sensor 148 corresponds to the intensity of light on a respective part of the main lens.

This means that the part of the image where pupil 74 is imaged will be composed of ERSs (one ERS for each lenslet receiving light from the pupil).

It can be shown that the image generated by this system and the images generated by systems 420 and 520 of FIG. 8 and FIG. 9 contain substantially the same information, only ordered differently: While the FIG. 10 system creates one large image of the subject, which is composed of smaller images showing the light received from the subject from slightly different locations, the FIG. 8/9 systems create many small images of the subject, each taken from a slightly different location. A transformation between each image type is possible by rearrangement of the pixels.

Sub-Sampling of the ERS

Embodiments of the present invention also comprise methods wherein instead of complete images of the ERS being acquired by array 148, sub-samples of the images are acquired. For these embodiments processor 24 analyzes the sub-samples to recover a complete ERS. Examples of such sub-sampling methods are described below.

The description of system 20 above assumes that aperture 140 is larger than ERS 130, so that a complete image of the ERS is acquired by array 148. In alternative embodiments of the present invention, aperture 140 is smaller than ERS 130, so that only a sub-sample of the ERS is acquired by the array. Multiple sub-samples of different regions of the ERS may be acquired by processor 24 varying the location and/or the size of aperture 140 in mask array 142.

Alternatively or additionally, sub-sampling may be implemented by using a fixed aperture 140 that is smaller than ERS 130, and moving, or effectively moving, source 62. (Moving the source while maintaining the aperture fixed is equivalent to keeping the source fixed while moving the aperture.) The source may be moved by any convenient mechanical method known in the art, such as by using a piezoelectric actuator. Alternatively, multiple individual sources may be switched to effectively move source 62.

Further alternatively, the processors of systems 420, 520, and 620 may be configured to analyze multiple ERSs originating from different parts of the same pupil 74. This is possible if the image of pupil 74 falls on more than one lenslet (in system 620), or on more than one pixel in each image of the subject (in systems 420 and 520).

Another system for analyzing multiple ERSs originating from the same pupil 74 may comprise a controllable aperture (similar to LCD mask 142 referred to above) combined with a standard camera. The aperture, which is smaller than the ERS, is configured to scan the ERS, and an image of the pupil 74 is taken at each aperture location.

The Appendix below describes the relation between the PSF and the distribution of intensities throughout the pupil. The information obtained from any of the four systems referred to above can be analyzed according to the Appendix to determine gaze direction.

Multiple ERS Systems

The descriptions above depict how one ERS is able to provide the gaze direction of the eye (left or right) of a subject. Some embodiments of the present invention include generating two or more ERSs for a single eye, and analyzing the individual ERSs to generate the gaze direction for the eye. Examples of such embodiments are described below.

Figure 11:
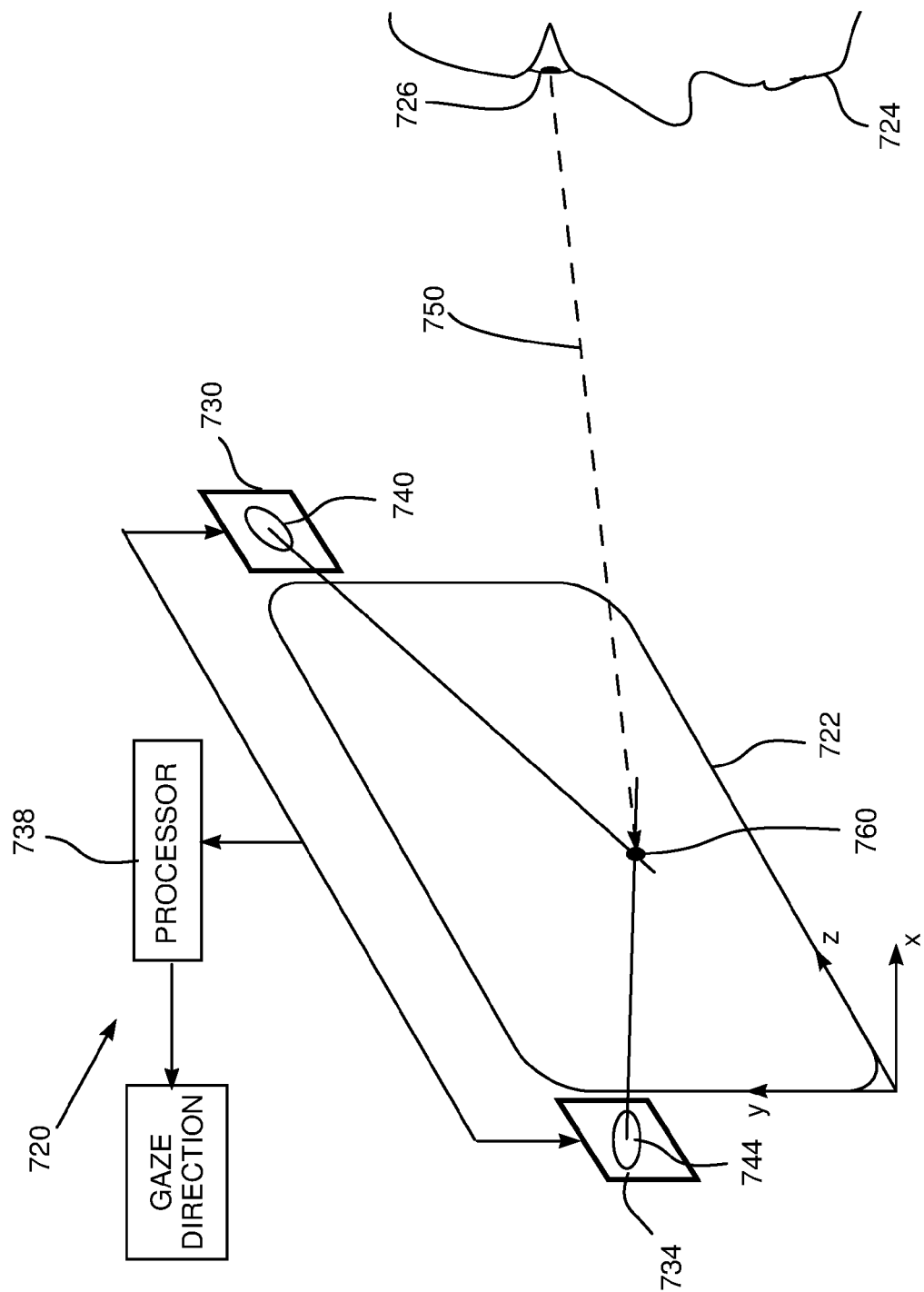
FIG. 11 is a schematic diagram of a gaze determining system, according to a disclosed embodiment of the present invention.

FIG. 11 is a schematic diagram of a gaze determining system 720, according to an embodiment of the present invention. In the figure, a screen 722 is being gazed at by a subject 724 in front of the screen. In the description herein edges of screen 722 are assumed to define a set of yz axes, and there is an x axis orthogonal to the computer screen. An eye 726 gazes at the screen, and there are two sensor assemblies 730, 734 located at known positions at sides of the screen in generally the same yz plane as the screen. Sensor assemblies 730, 734, may be selected from any of the sensor assemblies described herein, and may or may not be the same type of assembly. For example, assembly 730 could be similar to assembly 22 of system 20, and assembly 734 could be similar to assembly 222 of system 220. For clarity, in the following description sensor assemblies 730, 734 are both assumed to be similar to assembly 22, and both assemblies are operated by a common processor 738, which functions substantially as processor 24.

Assemblies 730, 734 illuminate eye 726, and respectively produce an ERS 740 and an ERS 744, depicted herein as ellipses 740 and 744 at the assemblies. As explained above with reference to FIGS. 5A, 5B, the major axes of the ellipses taken together with the eye optic center, or with the respective source light projection lines, define source planes, so that in this case there are two source planes. The two source planes intersect in a line 750, corresponding to the eye optic axis, so that processor 738 is able to evaluate the direction of the eye optic axis, and thus the gaze direction of the eye. From a knowledge of the gaze direction and the screen location, the processor is also able to evaluate a gaze point 760, the point on the computer screen at which the eye is looking. It will be understood that except for differences between the eye optic axis direction and its gaze direction, gaze point 760 corresponds to the intersection point of the major axes of the ERS ellipses.

The difference between the eye optic axis direction and the gaze direction may be resolved by a calibration process. Alternatively, both eyes of a subject may be measured, and the foveas of the subject may be assumed to be symmetrical with respect to their respective optic axes and to have no vertical offset. In this case, if the subject is looking approximately straight ahead, a mid-point between the two "gaze points" (which are different from the actual gaze point because the fovea is not on the optic axis) may be considered to be the actual screen gaze point 760.

Further alternatively, the horizontal and vertical offsets of the fovea of a subject with respect to its eye optic axis may be known or estimated, in which case the angle between the gaze direction and the eye optic axis may be calculated. Using this angle, the processor may adjust the gaze direction, and may also calculate the actual screen gaze point 760.

Figure 12:
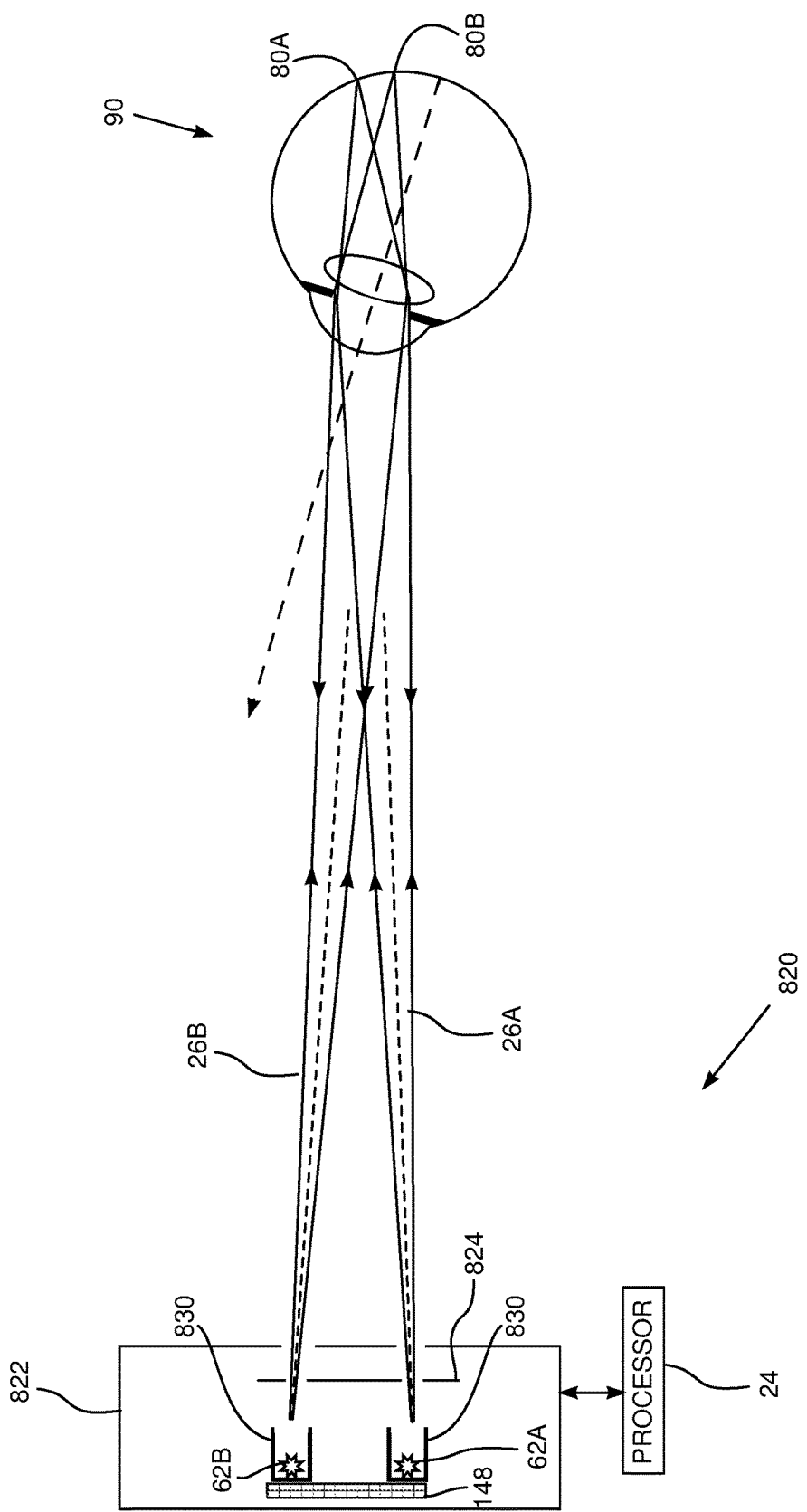
FIG. 12 is a schematic diagram of a gaze determining system.
Figure 13:
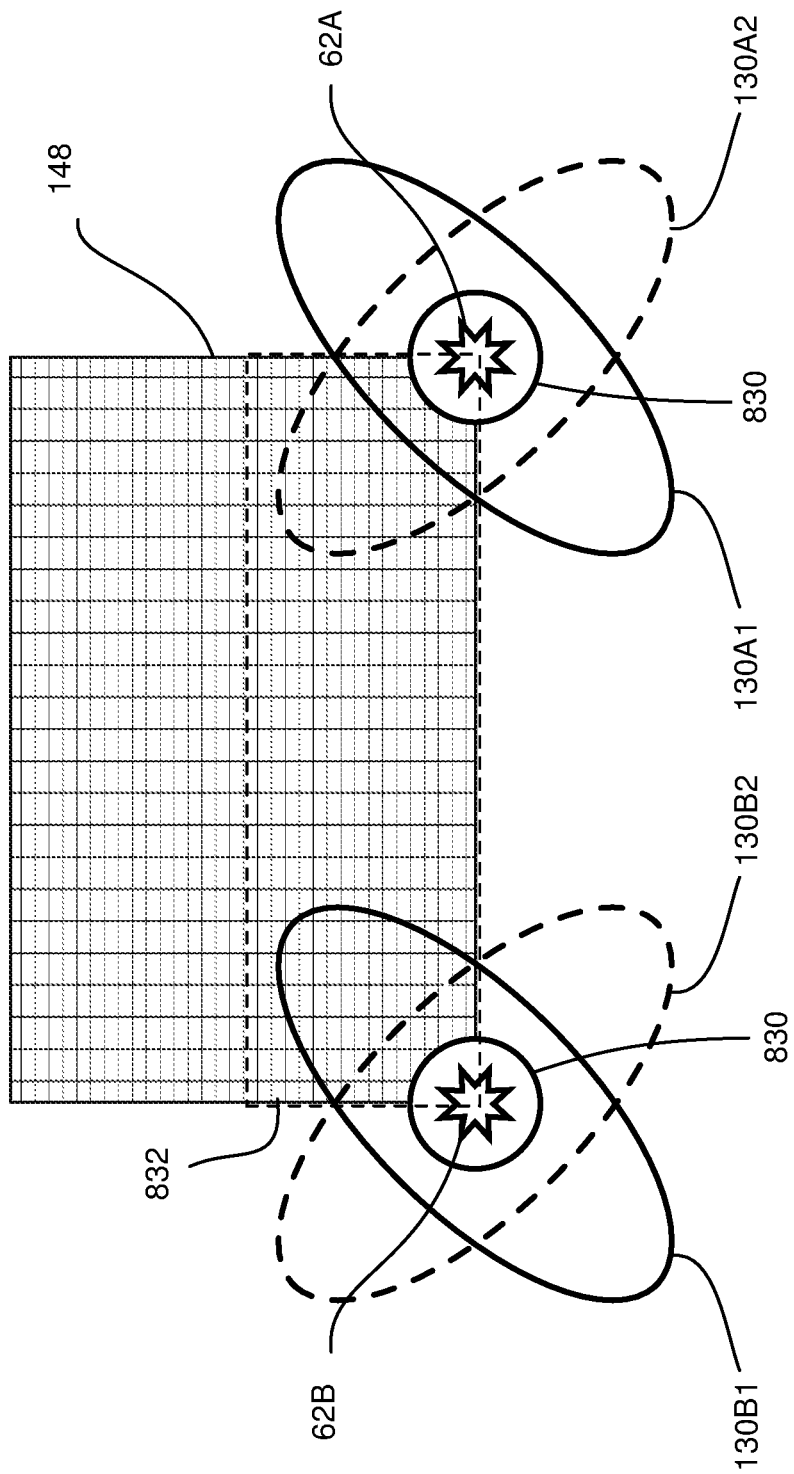
FIG. 13 is a schematic diagram of images formed on a sensor array of the system, according to a further disclosed embodiment of the present invention.

FIG. 12 is a schematic diagram of a gaze determining system 820, and FIG. 13 is a schematic diagram of images formed on a sensor array of the system, according to an embodiment of the present invention. System 820 may use sensor array 148 and two substantially similar sources 62A and 62B located at corners of the array, and the sensor and the sources are located in a sensor assembly 822. In some embodiments, within the sensor assembly a mask 824, generally similar to mask 142, provides controllable apertures for the sources and returning light.

The sources are shielded from radiating directly to the array by shields 830, and are configured to radiate respective projecting beams of light 26A and 26B to eye lens 90. Beam 26A forms a retinal image 80A of source 62A on the retina of the eye lens, and beam 26B forms a retinal image 80B of source 62B on the retina. The retinal images are retroreflected back to assembly 822, respectively being focused to an ERS on array 148 in proximity to source 62A, and to an ERS on the array in proximity to source 62B.

The presence of shields 830 prevents some portions of the ERSs being imaged by array 148, but since the ERSs are spread functions, other portions are imaged by the array, as is illustrated in FIG. 13. Sources 62A and 62B operate at the same time, and produce very similar ERSs, since the sources subtend very similar angles to the eye optic axis. Typically, for at least one of the ERSs, a substantial portion of the ERS falls on array 148 regardless of the angle made by the ERS with the array.

FIG. 13 illustrates ERSs falling on the array at two different times, at which the eye is oriented respectively at two different gaze angles. The ERSs at a first time are drawn as solid ellipses. The ERSs at a second time are drawn as broken ellipses. At the first time a substantial part of ERS 130B1, produced by source 62B, falls on the array. Only a small part of the corresponding ERS 130A1 produced by source 62A falls on the array.

The converse is true for the second time, where a substantial part of ERS 130A2, produced by source 62A, falls on the array. Only a small part of the corresponding ERS 130B2 produced by source 62B falls on the array.

Typically, processor 24 analyzes the most substantial portion of any imaged ERS, and derives the orientation, the size, and the ellipticity of the ERS considered as an ellipse, and thus the gaze direction of the eye, as is described above.

Consideration of FIG. 13 demonstrates that sensor array 148 may be reduced in size by approximately 50%, relative to the size of the array in system 20, since typically only a portion 832 of the array images both ERSs.

The embodiments described above illustrate combinations of elements of the present invention, and other combinations will be apparent to those having ordinary skill in the art.

Figure 14:
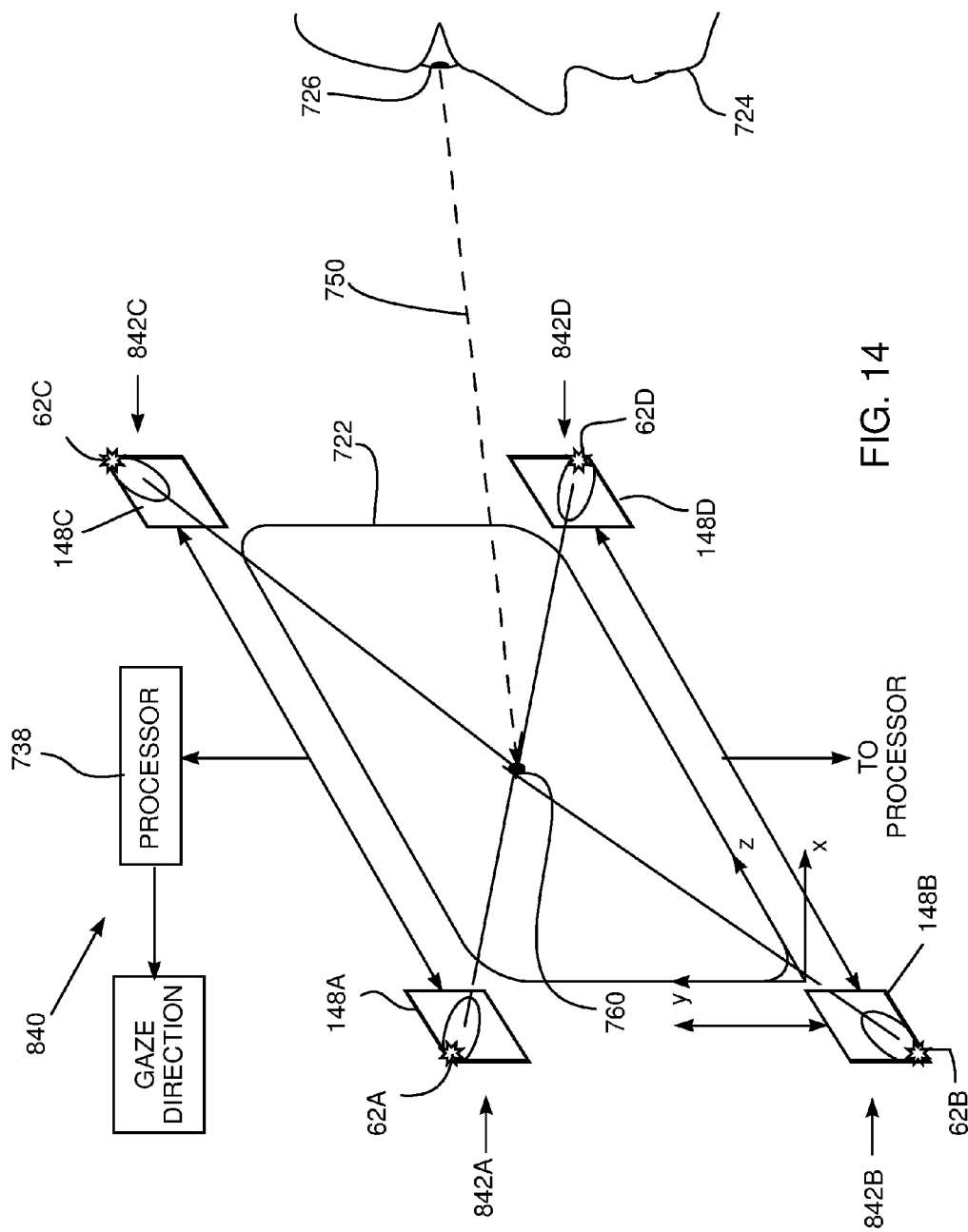
FIG. 14 is a schematic diagram of a gaze determining system, according to an embodiment of the present invention.

FIG. 14 is a schematic diagram of a gaze determining system 840, according to an embodiment of the present invention. Apart from the differences described below, the operation of system 840 is generally similar to that of system 720 (FIG. 11), and elements indicated by the same reference numerals in both systems are generally similar in construction and in operation.

System 840 has four sensor assemblies 842A, 842B, 842C, and 842D (selected from any of the sensor assemblies described herein) at the corners of screen 722, and all four sensor assemblies are operated by processor 738. Each assembly 842 has a respective array 148A, 148B, 148C, 148D, and a source 62A, 62B, 62C, and 62D is located, or effectively located, at the farthest corner of its array relative to screen 722. Having four sensor assemblies surrounding screen 722 ensures that while the screen is being gazed at there are at least two arrays which have well-defined ERS ellipses, or partial ellipses, with easily identifiable axes of symmetry. The two arrays are those that are the farthest from the gaze point, so having larger aberrations.

In system 840 there are four ellipse major axes, formed from respective ERSs, which generate planes intersecting at the optic axis of eye 726, so that processor 738 is able to determine a gaze direction of the eye. Since the screen gaze point 760 is on the screen, the ERS ellipse major axes also point towards the screen. By placing sources 62 at the farthest corner of their respective arrays, the arrays may be reduced in size, typically to 25% of the size of the array in system 20, while still ensuring that typically at least 50% of the ERS is incident on the array, and so is available to generate the ERS ellipse and to determine its parameters.

The embodiments described above typically use an axis of symmetry of the ERS in order to derive the gaze direction for a subject's eye. Alternative embodiments of the present invention do not use a geometric property of the ERS, such as the axis of symmetry referred to above, but rather analyze the intensity variation on array 148 of the ERS, or the intensity variation across a pupil imaged on the array, and relate the intensity variations to the gaze direction of the subject, as is explained in more detail below.

The ERS is a point spread function of a retinal image, which is itself a point spread function of the source. An Appendix (below) to the present disclosure provides an analysis for the intensity generated at the pupil of the eye, from the retinal image, and this intensity is a function of the retinal image. It will be understood that the ERS or the pupil image may be expressed functionally in a number of different ways. Herein, by way of example, the ERS or the pupil image is assumed to be functionally equivalent to an orthonormal set of two-dimensional functions such as the Zernike polynomials.

Figure 15:
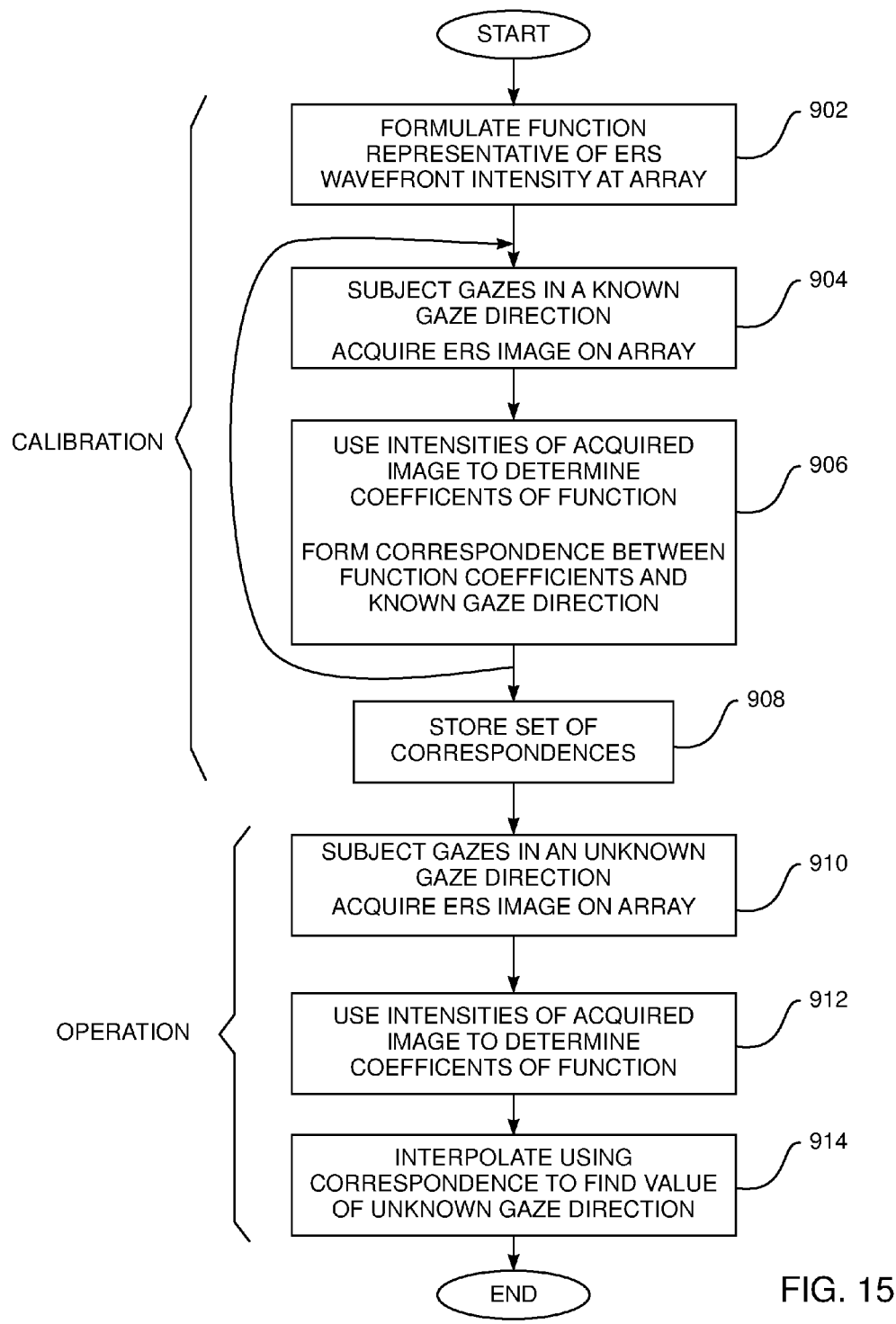
FIG. 15 is a flowchart of steps performed in determining the gaze direction of a subject, according to an embodiment of the present invention.

FIG. 15 is a flowchart of steps performed in determining the gaze direction of a subject, according to an embodiment of the present invention. The flowchart analyzes the intensity variations of the ERS, as generated on array 148, and from the analysis determines a gaze direction for the subject. For clarity, the description of the flowchart assumes gaze determining system 20 is being used, but those having ordinary skill in the art will be able to adapt the description, mutatis mutandis, for other gaze determining systems according to embodiments of the present invention.

In an initial step 902, a user of system 20 formulates a function representative of the ERS, as it is imaged on array 148. For clarity. the function is assumed to comprise a set of polynomials which, for any given ERS, have coefficients that reproduce the ERS.

In a first step 904 of a calibration stage of the flowchart a subject is asked to look in a known direction, for example at a specific point on a computer screen. While the subject is gazing at the point, array 148 acquires the ERS for the subject.

In an analysis step 906, processor 24 uses the intensities of the acquired ERS to determine optimal values of the coefficients of the polynomials selected in the initial step. The processor forms a correspondence between the coefficient values and the known gaze direction.

The calibration continues by steps 904 and 906 being repeated, for different known gaze directions, and in a final step 908 of the calibration stage, the processor stores the set of correspondences formed in step 906.

In an initial operation step 910 of the flowchart the subject looks in an unknown direction. While the subject is gazing in the unknown direction, array 148 acquires the ERS for the subject.

In an analysis step 912, the processor 24 uses the intensities of the acquired ERS to determine values of the coefficients of the same polynomials that were selected in the initial step.

In a final operation step 914, the processor compares the coefficient values of step 912 with the set of correspondences stored in step 906. The processor interpolates between the stored correspondences, to find interpolated coefficients that match the values found in step 912. The processor uses the interpolated coefficients to determine a value for the unknown gaze direction.

The description of the flowchart has assumed that an ERS is imaged on array 148. Those having ordinary skill in the art will be able to adapt the description, mutatis mutandis, for the case of the ERS being sampled so that effectively an eye pupil is imaged on the array, as is exemplified in system 620

(FIG. 10) above. The Appendix below describes in more detail how the intensities across a pupil vary.

In the descriptions above, the eye was assumed to have radial symmetry around the optic axis. Many people have eye defects which may damage this symmetry. The variations of a specific user may be studied during a calibration stage, and proper adjustments made during the later calculation of the gaze direction.

A person skilled in the art can adapt the systems above to track gaze direction of both eyes of the subject, or even of eyes of different subjects. For example in systems 420, 520, and 620, each pupil is imaged on different parts of the sensor, making extraction of each pupil's ERS straightforward.

Appendix

Analyzing Pupil Patterns

When the aperture in front of the imaging array is significantly smaller than the size of the ERS, the intensity of light returned from various parts of the pupil is sometimes not uniform. This non-uniformity may be explained using a ray-trace approximation of light propagation: Each point p, θ (as defined below) on the pupil refracts light from the light source (assumed to be a point) to a corresponding point on the retina r, α, implying a mapping transformation from the pupil coordinate system to the retina coordinate system: r(p, θ), α(p, θ).

The pupil coordinate system p, θ is a polar system with the center of the pupil at p=0, and the retina coordinate system r, α is also polar with r=0 at the mapping location of the center of the pupil, i.e. r(p, θ)=0. Typically, at r=0 the retinal PSF intensity will be maximal.

In the case of a perfect eye lens there will be no aberrations and the mapping will be trivial: r(p, θ)=0. However in the presence of aberrations some parts of the pupil will focus the light source poorly, causing the light rays to reach the retina at points different than r=0. Typically, the light intensity at these points is lower than at the PSF center.

Assuming a point-like aperture and point-like virtual light source that are positioned at the same location, then there is only one ray emanating from the retinal PSF that passes through both the pupil point p, θ and the aperture point. Since the virtual light source and aperture are both at the same position and point-like, that single ray follows the exact same path as the ray emanating from the light source, passing through the pupil point p, θ and being refracted to retina point r(p, θ), α(p, θ). Therefore the imaged intensity of a pupil point p, θ for a point-like aperture (in the ray trace approximation) is proportional to the retinal PSF intensity at r(p, θ), α(p, θ).

In the case where the physical aperture is smaller than the ERS but is not point-like, the light from the vicinity of r(p, θ), α(p, θ) will also pass the aperture. The pupil point intensity I(p, θ) in this case is proportional to convolving the retina PSF with a kernel h that is of the same shape and size as the aperture image at the retina. For a typical distance from the apparatus of 70 cm the magnification will be $$M = \frac{70}{1.7} \cong 40,$$

leading to a kernel the size of the aperture divided by M. The mathematical relation between the retinal PSF and the imaged intensity of the pupil is given by $$I(p,\theta) = \iint PSF(r',\alpha') \cdot h(r(p,\theta)-r', \alpha(p,\theta)-\alpha') dr' d\alpha'$$

Although the relation between pupil intensity and retinal PSF is complex, it is clear that, like the ERS, it is a manifestation of the eye's optical aberrations.

Analyzing Pupil Patterns While Moving the Light Source or Aperture

The pupil pattern analysis method can be combined with a method of moving the light source or aperture (such as is described above) since in both configurations it is desirable to have an aperture that is smaller than the ERS. Such a combined approach gives a method for evaluating the ray trace mapping r(p, θ), α(p, θ) between the pupil and retinal coordinates. The ray trace mapping information is equivalent to the eye's lens wavefront since the wavefront is orthogonal to the direction of the rays. The wavefront properties of the eye's lens give a complete optical description of the refractive properties of the eye's lens and therefore set an upper limit on the obtainable information regarding the refractive qualities of the eye's lens.

One way of obtaining the ray trace mapping is by finding the aperture location that maximizes intensity for a certain pupil position p, θ. Then a vector $\vec{D}$ is defined as the projection of the displacement, from the virtual light source to the aperture location, onto the plane perpendicular to the gaze direction. This displacement is directly mapped to a retinal displacement vector $(r_{\vec{D}}, \alpha_{\vec{D}}) = -\vec{D}/M$. Such a combined approach can lead to an evaluation of the eye's lens wavefront and a robust evaluation of the retinal PSF. The mathematical relation between the retinal PSF and the imaged intensity of the pupil is thus broadened to include also a displacement between the virtual light source and the aperture location. It is given by:

$$I(p,\theta,\vec{D}) = \iint PSF(r',\alpha') \cdot h(r(p,\theta)+r_{\vec{D}}-r', \alpha(p,\theta)+\alpha_{\vec{D}}-\alpha') dr' d\alpha'$$

Since r', α' are integration variables they can be replaced by:

$$r' \to r' - r(p,\theta) - r_{\vec{D}};\ \alpha' \to \alpha' - \alpha(p,\theta) - \alpha_{\vec{D}}$$

Leading to $$I(p,\theta,\vec{D}) = \iint PSF(r'-r(p,\theta)-r_{\vec{D}}, \alpha'-\alpha(p,\theta)-\alpha_{\vec{D}}) \cdot h(r',\alpha') dr' d\alpha'$$

Since PSF intensity is usually maximal at r=0 then choosing a small symmetric aperture implies that the maximal value of I(p, θ, $\vec{D}$) is obtained when: $r(p,\theta)+r_{\vec{D}}=0$ and $\alpha(p,\theta)+\alpha_{\vec{D}}=0$. Thus, if maximal I(p, θ, $\vec{D}$) is obtained at $\vec{D}^{max} = (D^{max}_r, D^{max}_\alpha)$ a mapping is given by:

$$r(\rho, \theta) = \frac{D_r^{max}}{M};\ \alpha(\rho, \theta) = \frac{D_\alpha^{max}}{M}$$

This information defines the wavefront properties of the eye's lens, as it provides the ray direction at any pupil point, and therefore defines the wavefront as the surface perpendicular to the ray direction at each pupil point.

Although the PSF can be computed from the wavefront information it can also be obtained directly from the data:

Combining the information obtained for $\vec{D}=0$:

$$I(p,\theta) = \iint PSF(r',\alpha') \cdot h(r(p,\theta)-r', \alpha(p,\theta)-\alpha') dr' d\alpha$$

which is equal to the intensity of the PSF(r(p, θ), α(p, θ)) blurred by the kernel h, allowing reconstruction of the full image of the blurred PSF. Applying a de-convolution filter (inverse of the kernel h) to the PSF blurred image will yield the image of the PSF. This PSF direct measurement method can be combined with the PSF calculated from the wavefront, yielding a robust method of PSF detection.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising the steps of:
   (a) illuminating an eye with projected light from a light source so as to cause a first image of the light source to be formed on a retina of the eye;
   (b) capturing reflected light returning from the first image on the retina, the capturing with a sensor so as to receive the first image on the sensor as at least a portion of a second image;
   (c) generating a signal corresponding to at least a portion of the second image, based on the first image; and
   (d) analyzing the signal to determine a gaze direction of the eye.

2. The method according to claim 1, wherein analyzing the signal comprises determining at least one line of symmetry in the at least portion of the second image.

3. The method according to claim 1, wherein analyzing the signal comprises forming a correspondence between the at least portion of the second image and an ellipse, and wherein determining the gaze direction comprises determining the direction in response to at least one of an ellipticity of the ellipse and an orientation of an axis of the ellipse.

4. The method according to claim 1, wherein capturing the reflected light comprises forming multiple images of a pupil of the eye on the sensor using a plurality of lenslets, and wherein analyzing the signal comprises deriving the second image from the multiple images of the pupil.

5. The method according to claim 1, wherein capturing the reflected light comprises:
   forming a single image comprising a pupil of the eye;
   splitting the single image into a plurality of sub-images using a plurality of lenslets; and
   capturing the sub-images with the sensor, and wherein analyzing the signal comprises extracting the second image from at least one of the sub-images comprising the pupil.

6. The method according to claim 1, wherein capturing the reflected light comprises using a focusing property of the eye to form the second image.

7. The method according to claim 1, and comprising:
   illuminating the eye with further projected light from a further light source so as to cause a third image of the further light source to be formed on the retina of the eye; and
   capturing the reflected light returning from the retina with the sensor so as to receive at least a portion of a fourth image of the third image on the sensor and so as to generate a further signal,
   wherein analyzing the signal comprises:
      analyzing at least one of the signal and the further signal in order to determine the gaze direction of the eye.

8. The method according to claim 1, and comprising:
   illuminating the eye with further projected light from a further light source so as to cause a third image of the further light source to be formed on the retina of the eye; and
   capturing the reflected light returning from the retina with a second sensor so as to receive at least portion of a fourth image of the third image on the second sensor;
   wherein analyzing the signal comprises:
      analyzing the signal and a second signal from the second sensor in order to determine the gaze direction of the eye.

9. The method according to claim 8, wherein analyzing the first and the second signals comprises determining at least a first line of symmetry in the third image and at least a second line of symmetry in the fourth image.

10. The method according to claim 9, and comprising deriving the gaze direction from an intersection of a first plane containing the first line of symmetry with a second plane containing the second line of symmetry.

11. The method according to claim 10, wherein the first plane contains a first line from the light source to an optical center of the eye, and wherein the second plane contains a second line from the further light source to the optical center of the eye.

12. The method according to claim 9, and comprising deriving a gaze point of the eye from an intersection of the first line of symmetry with the second line of symmetry.

13. An apparatus, comprising: a light source configured to illuminate an eye with light so as to cause a first image of the light source to be formed on a retina of the eye; a sensor which is configured to capture light returning from the retina so as to receive at least a portion of a second image of the first image on the sensor; and a processor which is configured to analyze a signal from the sensor in order to determine a gaze direction of the eye.

14. The apparatus according to claim 13, and comprising an aperture located in proximity to the second image.

15. The apparatus according to claim 13, and comprising a plurality of lenslets configured to form multiple images of a pupil of the eye on the sensor, and wherein analyzing the signal comprises deriving the second image from the multiple images of the pupil.

16. The apparatus according to claim 13, and comprising a plurality of lenslets configured to split a single image comprising a pupil of the eye into a plurality of sub-images, and wherein analyzing the signal comprises extracting the second image from at least one of the sub-images comprising the pupil.

17. The apparatus according to claim 13, and comprising: a further light source configured to illuminate the eye with light so as to cause a third image of the further light source to be formed on the retina of the eye, wherein the sensor is configured to capture the light returning from the retina so as to receive at least a portion of a fourth image of the third image on the sensor and so as to generate a further signal, and wherein the processor is configured to analyze at least one of the signal and the further signal in order to determine the gaze direction of the eye.

18. An apparatus, comprising:
   an image sensor defining a sensor plane;
   a plurality of lenslets located in proximity to the image sensor and arranged in a lenslet plane parallel to the sensor plane; and
   one or more light sources located in the lenslet plane.

19. The apparatus according to claim 18, wherein the lenslets have a focal length selected so that an image of a subject illuminated by the light source is focused on the image sensor.

20. The apparatus of claim 18, wherein the one or more light sources located in the lenslet plane, comprise:
 a partial reflector located in proximity to the plurality of lenslets; and
 a light source configured to transmit light to the partial reflector and located at a position that reflects in the partial reflector to the lenslet plane.

* * * * *